United States Patent [19]

Kidd et al.

[11] Patent Number: 4,712,558

[45] Date of Patent: Dec. 15, 1987

[54] ELECTRICAL STIMULATION OF MUSCLE

[75] Inventors: Geoffrey Kidd, Liverpool, England; Daniel V. Maher, Ennis, Ireland; Jozef Cywinski, Bronx, N.Y.

[73] Assignee: Bio Medical Research Ltd., Ireland

[21] Appl. No.: 710,839

[22] Filed: Mar. 12, 1985

[30] Foreign Application Priority Data

Mar. 13, 1984 [GB] United Kingdom ................ 8406509

[51] Int. Cl.$^4$ .............................................. A61N 1/36
[52] U.S. Cl. .................................................. 128/421
[58] Field of Search ............................... 128/421–422, 128/419 PG

[56] References Cited

U.S. PATENT DOCUMENTS

| | | | |
|---|---|---|---|
| 3,727,616 | 4/1973 | Lenzkes | 128/419 E |
| 4,165,750 | 8/1979 | Aleev et al. | 128/422 |
| 4,255,790 | 3/1981 | Hondeghem | 364/487 |
| 4,338,945 | 7/1982 | Kosugi et al. | 128/421 |
| 4,390,023 | 6/1983 | Rise | 128/421 |
| 4,408,609 | 10/1983 | Axelgaard | 128/421 |
| 4,499,900 | 2/1985 | Petrofsky et al. | 128/423 W |
| 4,505,275 | 3/1985 | Chen | 128/421 |
| 4,528,984 | 7/1985 | Morawetz et al. | 128/421 |
| 4,598,713 | 7/1986 | Hansjürgens | 128/421 |

FOREIGN PATENT DOCUMENTS 81209 6/1983 European Pat. Off. ..... 128/419 PG

Primary Examiner—William E. Kamm
Attorney, Agent, or Firm—Paul J. Sutton

[57] ABSTRACT

A method and apparatus are disclosed for the electrotrophic stimulation of muscle, that is, stimulation using pulses trains onto which information which will cause long-term functional and/or structural changes in the muscle tissue. This information is coded onto the interval between successive pulses of the series. Also disclosed is a method and apparatus for acquiring trophic data from motor unit action potential series.

37 Claims, 32 Drawing Figures

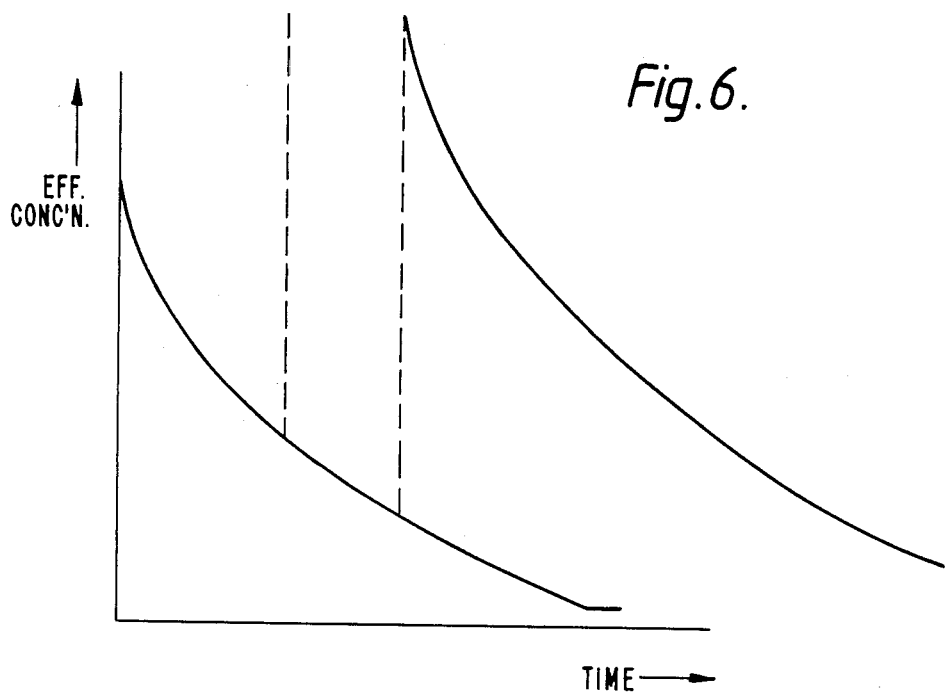
Fig.6.

```
PROGRAM SERVICEROMDATA;

USES APPLESTUFF ;

TYPE ROM = ARRAY [ 0..511 ] OF INTEGER ;

VAR ERROR : INTEGER ;
    DATA  : ROM ;

PROCEDURE SETVIA ; EXTERNAL ;

PROCEDURE PULSES ( VAR ERROR : INTEGER ; VAR DATA : ROM ) ;
EXTERNAL ;

PROCEDURE GETROMFILE ;
VAR G:FILE OF INTEGER;
    NAME : STRING ;
    I : INTEGER ;
BEGIN
  WRITELN ( 'DATA FILE NAME <.ROM> ? ' );
  READLN (NAME);
  RESET ( G,NAME );
  WRITE ('SETTING UP DATA ARRAY ..');
  FOR I := 0 TO 511 DO BEGIN
  DATA[I] :=G  ;
  GET (G)
  END;
  WRITELN ( 'DONE ' );
  CLOSE ( G )
END;

BEGIN

PAGE(OUTPUT);

SETVIA ;

GETROMFILE ;

REPEAT

WRITE ( '.',CHR(7));

PULSES ( ERROR , DATA )

UNTIL (ERROR<>0 ) OR KEYPRESS ;

IF ERROR<>0 THEN WRITELN('?? ERROR ',ERROR);

END.
```

*Fig. 13A.*

```
PROGRAM SETUPENCODEDDELAYS;

TYPE ROM   = ARRAY [ 0..1023 ] OF INTEGER;

VAR DATA : ROM ;

PROCEDURE CODEROMWORD (VAR DATA :INTEGER;
                COUNT,  CHAN : INTEGER;
                NEEDPULSE, CHANOFF :BOOLEAN ) ;

VAR I : INTEGER ;
BEGIN
(* THE SIXTEEN BITS ARE :- (0..15 CONVENTION )
    15  SET TO 0 IF CHANNEL IS ON
    14  SET TO 1 IF PULSE REQUIRED
    13  THE NEXT 4 BITS ARE CHANNEL NUMBER
    12
    11
    10  ..L S B OF CHANNEL NO.
     9
     .
     .
     .
     0  10 BIT COUNT
*)
  IF NEEDPULSE THEN I:=16384 ELSE I:=0 ;
  IF CHAN > 07 THEN WRITELN('??? CHAN TOO BIG ',CHAN );
  IF COUNT>1023THEN WRITELN('???COUNT TOO BIG ',COUNT);
  IF := I + CHAN * 1024 ;
  I := I + COUNT ;
  IF CHANOFF THEN BEGIN
    I:=-1 ;
    WRITELN( 'CHANNEL ',CHAN,' OFF')
  END;
  DATA := I
END;

PROCEDURE PUTROMFILE ;
VAR I : INTEGER ;
    G : FILE OF INTEGER ;
    NAME : STRING ;
BEGIN
  WRITELN ;
  WRITELN('DESTINATION FILE NAME <.ROM> ? ' );
  READLN (NAME);
  READLN (NAME);
  REWRITE ( G, NAME ) ;
  WRITELN('SAVING ROM DATA ...');
  FOR I := 0 TO 511 DO BEGIN
    G↑:= ADATA[I] ;
    PUT (G);
    (*
    WRITELN(I,' ',DATA[I],' ',((DATA[I]DIV 1024) MOD 16),' ',
         (DATA[I] MOD 1023))
    *)
  END ;
  WRITELN ('DONE ');
  CLOSE ( G, LOCK)
END;
```

*Fig. 13B.*

```
PROCEDURE GETDATAFILE ;
VAR COUNT, CHAN, OLDCHAN, I, J : INTEGER;
    F : TEXT ;
    NAME : STRING ;
BEGIN
  WRITELN;
  WRITELN('SOURCE FILE NAME <.TEXT> ? ') ;
  READLN (NAME ) ;
  RESET ( F, NAME ) ;
  FOR I :=0 TO 511 DO DATA[I] := -1 ;
  OLDCHAN := -1;
  READ(F,CHAN);
  WHILE (CHAN <> -1) AND (NOT EOF(F)) DO BEGIN
    IF CHAN <> OLDCHAN THEN BEGIN
      COUNT :=0 ;
      OLDCHAN := CHAN;
      J := 64 * CHAN
    END;
    FOR I := J TO J+7 DO BEGIN
     READ ( F,DATA[I] ) ;
     WRITELN('CHAN ',CHAN,' INTERVAL ',DATA[I],'INDEX ',I)
    END;
    READLN ( F ) ;
    READ(F,CHAN);
    J := J + 8 ;
    IF COUNT > 63 THEN WRITELN('?? TOO MANY PULSES ON CHANNEL ', CHAN )
  END;
  CLOSE (F)
END;

PROCEDURE ENCODEINTOROM ;
CONST NEED = TRUE ;
      OFF  = FALSE;
VAR CHAN, J,K, DELAY, OFFSET : INTEGER :
BEGIN
  WRITELN('CALCULATING ENCODED VALUES .. ');
  FOR CHAN := 0 TO 7 DO BEGIN
    OFFSET := 64 * CHAN ;
    FOR J := 0 TO 63 DO BEGIN
     K := OFFSET+J ;
     DELAY := ROUND ( DATA[K] / 2 + 0.1 );
(*
WRITELN(K,' ',DATA[K],' ',DELAY,' CHAN ',CHAN);
*)
     (* DATA CONTAINS THE DELAY IN MSEC
       THE DATA FOR THE ENCODED ROM DATA HAS A
       RESOLUTION OF 2 MSEC HENCE THE DIVISION BY
       TWO. EG A DELAY OF 16 MSEC BECOMES A COUNT OF 8
       NOTE THAT A DELAY OF 15 MSEC IS ALSO A COUNT OF 8
     *)
     IF DELAY > 0 THEN CODEROMWORD ( DATA[K], DELAY, CHAN, NEED,OFF ) ;
     (* THE DATA ARRAY ALREADY CONTAINS -1 WHICH IS THE SIGNAL FOR
       CHANNEL OFF TO THE ASSEMBLER OUTPUT ROUTINES
     *)
     END
    END;
   WRITELN ( 'DONE CALCULATING ENCODES VALUES' )
END;
```

Fig.13C.

```
BEGIN
   PAGE (OUTPUT);
   GETADATAFILE;
   ENCODEINTOROM;
   PUTROMFILE
END.
```

Fig. 13D.

```
        LDA;   @
  .MACRO POP
    PLA %1
    PLA
    STA %1+1
  .ENDM

.MACRO PUL
    LDA %1+1
    PHA
    LDA %1
    PHA
  .ENDM
;
;CONSTANTS FOR THE PROGRAM
;
MXCHAN .EQU 7 ; 8 CHANNELS 0..7
;
;
;PAGE ZERO USE
;
RETURN   .EQU 0;
TEMP     .EQU RETURN+2
CHAN2    .EQU TEMP+2
ERROR    .EQU CHAN2+2
ERRORP   .EQU ERROR+2
CHAN     .EQU ERROR+2
ROMP     .EQU CHAN+2
ROMTAB   .EQU ROMP+2
WORK     .EQU ROMTAB+10 ; 16 BYTES FOR ROM POINTERS
CHANTB   .EQU WORK+10 ; 16 BYTES FOR WORK AREA
;
;VIA AT SLOT 2
;
SLOT     .EQU OCOAO ; SLOT 2
VIAB     .EQU SLOT
VIAA     .EQU SLOT+1
DDRB     .EQU SLOT+2
DDRA     .EQU SLOT+3
TICLRF   .EQU SLOT+4
TI1L     .EQU SLOT+4
TI1H     .EQU SLOT+5
ACR      .EQU SLOT+OB
IFR      .EQU SLOT+OD
IER      .EQU SLOT+OE
;
;
```

Fig.13E.

```
;          .PROC SETVIA,0 ;NO PARAMETERS
;          *************
;SET UP THE VIA (SLOT2) FOR OUTPUT
;
;
SETUP LDA#OFF
      STA DDRA
      STA DDRB
      STA VIAB ; SET B SIDE HIGH
      ;
      LDA # 7F
      STA IER ; DISABLE ALL VIA INTERRUPTS
      SEI
      ;
      LDA # 040 ; MAKE TIMER1 FREE RUNNING
      STA ACR   ; WITH NO OP ON BIT7 OF B SIDE
      ;
      LDA # 0
      STA VIAA ; SET A SIDE LOW
      STA TI1L ; SET UP THE TIMER
      LDA # 08 ; FOR 2048 PULSES = 2048/1024 MS
      STA TI1H
      RTS
      ;
```

*Fig. 13F.*

```
;          .PROC SETVIA,0 ;NO PARAMETERS
;          *************
;SET UP THE VIA (SLOT2) FOR OUTPUT
;
;
SETUP LDA#OFF
      STA DDRA
      STA DDRB
      STA VIAB ; SET B SIDE HIGH
      ;
      LDA # 7F
      STA IER ; DISABLE ALL VIA INTERRUPTS
      SEI
      ;
      LDA # 040 ; MAKE TIMER1 FREE RUNNING
      STA ACR  ; WITH NO OP ON BIT7 OF B SIDE
      ;
      LDA # 0
      STA VIAA ; SET A SIDE LOW
      STA TI1L ; SET UP THE TIMER
      LDA # 08 ; FOR 2048 PULSES = 2048/1024 MS
      STA TI1H
      RTS
      ;
```

*Fig. 13G.*

```
        .PROC PULSES ,2 ; 2 PARAMETERS
;         *************  (VAR ERROR:INTEGER;
;                       VAR ROM: ARRAY OF INTEGER
;
; SERVICE EACH CHANNEL
; UNTIL ALL OFF OR ERROR
;
      JMP START
;
;
SAVEZ   .BLOCK 256,0 ; SPACE FOR PAGE ZERO
;
START POP RETURN
      POP ROMTAB
      POP ERRORP
      JSR MOVOUT ; SAVE PAGE ZERO
      LDA ROMTAB
      STA ROMP
      LDA ROMTAB+1
      STA ROMP+1
      LDA # 0
      LDY # 0
      STA @ERRORP,Y
      INY
      STA @ERRORP,Y ; INITIALSE TO NO ERROR
      JSR TABLE ; INIT POINTERS TO ROM
      JSR SETALL ; SET COUNTS FROM THE ROM
      JSR SETPAT ; SET OUTPUT PATTERNS FOR THE VIA
MORE LDA#7  ; INITIALISE
      STA CHAN  ; CHANNEL COUNT
;
      LDA # 40
SYNCH BIT IFR  ; HAS TIMER1 COUNTED DOWN
      BEQ SYNCH
      ;
      LDA TICLRF ; CLEAR TIMER1 INTERRUPT FLAG
;
MAIN LDX # 0D  ; ANY CHANNELS ON ?
               ; 16 BYTES (8 CHANNELS)
      LDA#80 ; SET THE TOP BIT
SC1 AND WORK+1,X
      DEX
      DEX
      BPL SC1
; SCAN TO SEE IF ANY CHANNELS ON
; CHECK BIT 15 IF 0 THEN ON
;
      ASL A
      BCS DONE
      JSR SERVE ; SERVICE THE CURRENT CHANNEL
      LDA ERROR
      CMP # 0
      BNE WOOPS
      DEC CHAN ; CHAN IS ANDED IN SERVE
      BPL MAIN
      ;
      JMP MORE
      ;
      ;
WOOPS LDY#0
      STA @ERRORP, Y ; SAVE ERROR NO
      INY
      LDA CHAN   ; AND THE CHANNEL
      STA @ERRORP,Y
;              DIAGNOSTICS COMMENTED OUT
;     JSR DIAG
```

*Fig.13H.*

```
DONE JSR MOVBAK
     PUL RETURN
     RTS
     ;
;
; SETPAT
; SET THE PATTERNS FOR THE VIA
; BIT0 TO BIT7
;
SETPAT LDA # 80
     LDX # 7
SET1  STA CHANTB,X
     LSR A
     DEX
     BPL SET1
     RTS
;
;
SERVE LDA CHAN
    ASL A   ; TWO BYTES PER WORK VARIABLE
    STA CHAN2 ;
    TAX     ; X POINTS TO WORK AREA
    LDA WORK+1,X ; NOW SEE IF CHANNEL ON
    ASL A
    BCC OK
;
EXIT RTS
;
;
;

;
OK DEC WORK,X; DECREMENT THE CURRENT COUNT
    BNE EXIT
    LDA WORK+1,X
    AND # 3    ; ONLY 2 BITS ARE THE MSB OF THE COUNT
    BEQ MAYPULSE
    DEC WORK+1,X; IF NOT PULSE NEED TO DECREMENT MSB
    JMP EXIT
MAYPULSE LDA WORK+1,X
    ASL A
    ASL A    ; SEE IF PULSE REQUIRED
    BCC EXIT
;
;OUTPUT A PULSE
;
```

Fig.13I.

```
;
;
;OUTPUT A PULSE
;
;SEE IF CHAN CORRESPONDS WITH THAT IN WORK DATA
PULSE LDA WORK;1,X ;THE MSB OF THE DATA WORD
      LSR A
      AND # OE ; MOVE THE CODED CHAN INTO BOTTOM
      CMB CHAN2
      BEQ POK
      LDA # 1;
      STA ERROR
      RTS
;HAVE JUST CHECKED THE
;CURRENT CHANNEL DATA AGAINST THAT
;CODED INT THE COPY OF THE WORK AREA
;
;NOW PULSE CHANNEL A UP DOWN
;AND CHANNEL B DOWN UP
;
POK LDX CHAN
    LDA CHANTB,X
      STA VIAA  ; 4
      EOR#0FF ; INVERT BYTE
      STA VIAB
      LDA#0    ; 2
      STA VIAA; 4
      LDA# 0FF
      STA VIAB;
;
;
;GET THE NEXT COUNT FROM ROM
;AND RETURN
;
;GETCNT
;GET COUNT FROM ROM
;A POINTS TO CHAN
;POINTER IN PAGE ZERO UPDATED FOR NEXT ENTRY
;
GETCNT LDX CHAN2
       LDA @ROMTAB,X
       STA WORK,X
;INCREMENT POINTER INTO ROM
       INC ROMTAB,X
       BNE GET1
       INC ROMTAB+1,X
;
GET1 LDA @ROMTAB,X
     STA WORK+1X
;INCREMENT POINTER INTO ROM
       INC ROMTAB,X
       BNE GET2
       INC ROMTAB+1,X
;
GET2 RTS
;
    ;
    ;
;MOVBAK COPY BACK ALL OF PAGE ZERO
```

Fig. 13J.

```
; MOVBAK COPY BACK ALL OF PAGE ZERO
MOVBAK LDX # 0
M2     LDA SAVEZ,X
       STA O,X
       INX
       BNE M2
       RTS
    ;
;MOVOUT COPY ALL OF PAGE ZERO
MOVOUT LDX # 0
M1     LDX O,X
       STA SAVEZ,X
       INX
       BNE M1
       RTS
    ;
    ;
    ;
    ;SETALL COUNT FROM ROM
    ;
SETALL LDY#0
ST1    TYA
       ASL A
       STA CHAN2
       JSR GETCNT
       INY
       CPY # 08
       BNE ST1
       RTS
       ;
;
; TABLE
; SET TABLE OF POINTER INTO THE ROM
; ROMTAB IS POINTER ALREADY SET UP
;
TABLE LDA ROMTAB
      STA TEMP
      LDA ROMTAB+1
      STA TEMP+1
      LDY # 07
      LDX # 2
TAB1 CLC
      LDA TEMP
      ADC # 80 ; 128 BYTES PER CHAN
      STA TEMP
      STA ROMTAB,X ; STORE IN PAGE ZERO
      LDA TEMP+1
      ADC # 0
      STA TEMP+1
      LMX
      STA ROMTAB,X
      INX       ; FOR NEXT TIME
      DEY
      BNE TAB1
      RTS
```

*Fig. 13K.*

ELECTRICAL STIMULATION OF MUSCLE

DESCRIPTION

The present invention relates to the electrical stimulation of muscles.

In the past, a number of methods and apparatuses have been developed for so-called Faradic stimulation of muscle tissue with a view to obtaining beneficial effects, such as the improvement of muscle tone. Faradic stimulation has generally proceeded on the basis of applying to muscle, usually by a number of electrodes overlying the muscle or muscles in question, an electrical signal to produce a mechanical response in the fibres of the muscle intended to be similar, on qualitative and approximate assessment to that caused by the fibres' stimulation by associated motor neurons. To attempt to achieve this, the electrical signal has usually been a pulse train, having uniform characteristics in terms of pulse length and pulse separation, intended to stimulate the fibres in a manner similar to their stimulation by their associated motor neurons. Such a pulse train, properly applied, produces contraction of the muscle fibres resulting in mechanical action. By applying the pulse train in bursts, a series of contract/relax actions are produced as an attempt to minimise the discomfort arising from the indiscriminate form of stimulation. However, partly due to the unnatural pattern of the applied stimuli, the resultant effects have generally been neither as beneficial nor as long lasting as might be hoped. By a refined and discriminating recording technique and by suitable signal processing techniques, one can extract from the recorded electromyographic response of a muscle, which usually comprises motor unit action potentials (MUAPs) associated with a multiplicity of motor units, the MUAPS associated with individual motor units. This may be achieved, for example, by pulse height and pulse shape analysis of individual pulses making up the electromyogram. Conveniently, the signal processing involves pulse height analysis, since it has been found that by defining a suitably narrow pulse height detection window (of 12 microvolts in one practical example), MUAPs associated with individual motor units can be monitored.

Conventional Faradism has proceeded on the basis that the integrated mechanical response of a muscle is a function of the mean frequency of MUAPs applied to its constituent motor units. This justified the conventional Faradic technique of attempting to control muscular contraction and relaxation by applying bursts of pulses, the pulses in the bursts being of a frequency intended to produce the desired degree of subjectively assessed contraction. The assumption has been, however, that the required contraction of muscle fibres is the only information coded onto MUAPs According to an aspect of the invention apparatus for the stimulation of muscle fibre by the application of a stimulating electrical signal to the muscle fibre or to overlying tissue, comprising control means, pulse generating means for generating an electrical signal for use as said stimulating electrical signals and whose waveform carries information which affects the response of said muscle fibre to its stimulation by said signal and at least one pair of electrodes to be placed, in use, in electrical contact with the muscle fibre or overlying tissue, the pulse generating means being responsive in use to the control means to generate as said stimulating electrical signal a sequence of electrical pulses whose characteristics code for electrotrophic information thereby to convey electrotrophic information to the muscle fibre to bring about an electrotrophic response in said muscle fibre for effecting change in the muscle fibre to cause desired structural and/or functional adaptation of the muscle, and to supply the sequence of electrical pulses so generated to the said at least one pair of electrodes, which electrodes transmit the sequence of electrical pulses supplied by the pulse generating means to the muscle fibre or overlying tissue to impart thereto the electrotrophic stimulation to effect the desired structural and/or functional adaptation of the muscle.

This aspect of the invention also provides a method of applying stimulating pulses to muscle fibre comprising generating and applying fibres or to overlying tissue a stimulus pulse sequence being so selected that the pulse sequence conveys electrotrophic information for causing a desired structural and/or functional adaptation of muscle fibre and of which a muscle is comprised and applying said sequence of pulses to the muscle, or to overlying tissue.

Investigation of muscle by new techniques has led to an appreciation of the fact that there is information encoded into the MUAP discharge sequence which is apparently redundant to the required mechanical response of the muscle fibres. Thus in the operation of a normal muscle, the frequency analysis of the MUAPs gives two elements of information. The first, previously assumed to be the only information, is required to generate the force needed to effect a movement, and the second is a different signal, apparently redundant mechanically, but in fact of great importance in generating an intracellular (muscle fibre) environment conducive to biosynthesis. The two elements of information "time share" in the nerve discharge but can be extracted by a form of time series analysis such as "favoured pattern analysis" used in applications of communication theory. The second element of information is believed to initiate and control functional adaptation of the muscle fibre. This second element can be identified from the difference in discharge patterns in muscles adapted to one form of muscle activity and the same muscles adapting to another where, for example, an anabolic "body-building" procedure is taking place. At present, the information conveyed by this code is by no means fully understood. Nevertheless it can be copied and transcribed and so used to define a pulse sequence for use in muscle stimulation with a view to alleviating muscular disfunction and/or otherwise "re-educating" muscles to produce medium and long term beneficial effects by effecting a long lasting metabolic change in the muscle being treated which manifests itself by its contractile properties.

To facilitate the generation of a muscle stimulating signal conveying useful trophic information, a third aspect of the invention provides apparatus for applying stimulating pulses to muscle fibre comprising pulse generating means and at least one pair of electrodes for applying a sequence of pulses generated thereby to the muscle fibre, or to overlying tissue, the pulse generator being so adapted that the intervals between respective stimulating pulses in a sequence of pulses can be individually defined.

The second aspect of the invention further provide a method of generating a sequence of muscle stimulating pulses in accordance with pulse interval data held a memory comprising the steps of (A) reading out an item of pulse interval data from said memory;

(B) initializing the contents of a memory location with data representing a count;

(C) periodically incrementing or decrementing said contents;

(D) periodically testing said contents and repeating (C) until said contents have a value determined in relation to the pulse interval data such that the number of repeats of (C) is determined by the pulse interval data; and (E) generating a stimulating pulse when said value occurs;

steps (A) to (E) inclusive being executed for each of a series of items of pulse interval data.

Suitably in step (B) the contents of the memory location are initialized with the value of the item of pulse interval data and wherein the loop from step (D) to step (E) is exited when said contents have a predetermined value. A plurality of channels of stimulating pulses may be produced, in which case steps (A) to (E) inclusive may be carried out for each channel, corresponding steps for each channel being carried out in succession. Prior to generation of each pulse, a check may be carried out to establish if the pulse should be produced, and the pulse inhibited if it should not e.g. because no pulse is required at that time, or a hardware or software fault is detected.

In the second aspect of the invention, electrotrophic stimulation may be combined, preferably in a non-overlapping manner time-wise, with functional stimulation to provide a treatment procedure for regenerating muscle and/or improving its performance. Thus this aspect of the invention also provides apparatus for the stimulation of muscle fibre by the application of a stimulating electrical signal to the muscle fibre or to overlying tissue, comprising control means, pulse generating means for generating an electrical signal for use as stimulating electrical signals and whose waveform carries information which affects the response of said muscle fibre to its stimulation by said signal and at least one pair of electrodes to be placed, in use, in electrical contact with the muscle fibre or overlying tissue, the control means selectively controlling, in use, the pulse generating means to generate a said stimulating electrical signal a sequence of electrical pulses whose characteristics code electrotrophic information thereby to convey electrotrophic information to the muscle fibre to bring about an electrotrophic response in said muscle fibre for effecting change in the muscle fibre to cause desired structural and/or functional adaptation of the muscle, or a sequence of electrical pulses whose characteristics code Faradic information to convey Faradic information to the muscle fibre to bring about a Faradic response in said muscle fibre and to supply the sequence of electrical pulses so generated and coding the stimulating information to the said at least one pair of electrodes, which electrodes transmit the sequence of electrical pulses supplied by the pulse generating means to the muscle fibre or overlying tissue to effect the desired structural and/or functional adaptation of the muscle or the Faradic stimulation respectively.

The invention will be further described by way of example with reference to the accompanying drawings in which:

FIG. 6 illustrates the cycle of agents effective in muscle fibre metabolism;

FIGS. 13A to 13K are a listing of software used in the embodiment of FIG. 12;

FIG. 1A shows the differing time courses for recovery of nerve, muscle fibre action potential and muscle fibre mechanical response make it possible to fuse the mecahnical responses by stimulating electrically at a sufficiently high frequency, (FIG. 1B). This is the basis of Faradism.

FIG. 2 shows the temporary and transient effects of electrical stimulation at high frequency gave an augmentation of muscular force which was erroneously believed to justify forms of Faradic stimulation as clinical therapy.

Figure 1A:
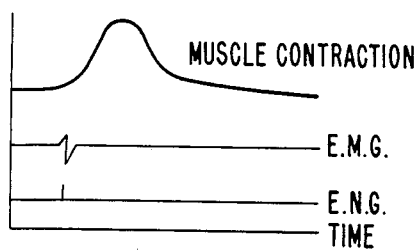
FIGS. 1A and 1B illustrate the mechanical response and the recovery of nerve and consequent muscle fibre action potential of a muscle.

Conventional, Faradic stimulation is stimulus dominated. It was well known that an electrical stimulus of adequate strength would excite a motor nerve within a muscle, or the muscle fibres themselves if they were denervated, and give responses of three sorts as shown in FIG. 1A. The signal of action in the motor nerve (the electroneurogram, ENG), the signal of action in the muscle fibres (the electromyogram EMG) and some force record of the muscle's mechanical response (the trace of muscle contraction).

Figure 1B:
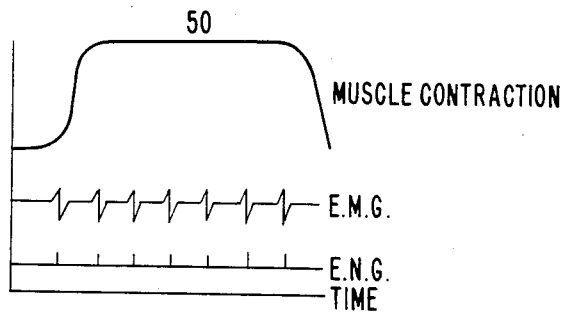

Because of the very rapid recovery of the nerve from a single action and the less but still rapid recovery of the electrical effects of action in the muscle fibre, the mechanical consequencies of repeated electrical stimulation can summate mechanically. FIG. 1B shows 50 stimuli per second generating a mechanical response with the whole effect fusing. Note that the electrical effects in the nerve (ENG) and muscle (EMG) are still separate.

Figure 2:
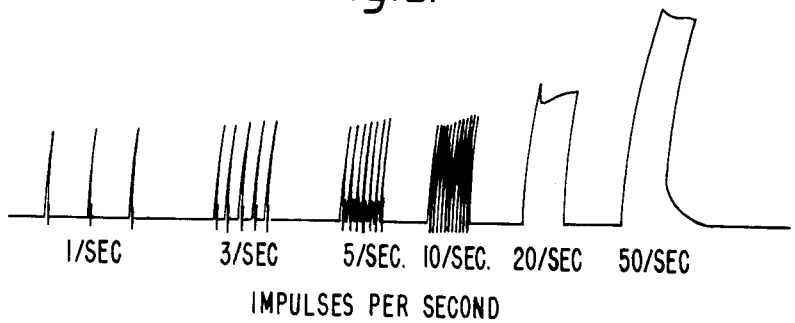
FIG. 2 shows the mechanical response of a muscle to stimulation of increasing frequency.

As stimulation at increasing frequencies (FIG. 2) yielded an augmentation of force (the amplitude of the mechanical trace) it was conventionally assumed that this form of stimulation would have beneficial therapeutic effects. This has not in general been found to be so. The augmentation of force was due to the increased acid reaction within the muscle fibres, which was a short lasting effect, and to a local increase in muscle temperature which was similarly transient. Unphysiological responses were being generated by unnatural forms of electrical stimulation.

As the analytical approach to muscular activity progressed from the activity of the muscle as a whole (a) to aggregates of muscle fibres (b) and lately to the activity of single muscle fibres (c) an understanding of the trophic code influencing the structural adaptation of a muscle to natural activity and, more importantly, to electrical stimulation became feasible.

There are five significant stages involved in linking the excitation of a muscle nerve to the generation of force by the muscle and its subsequent recovery from action and the preparation for the next phase of activity:
(i) the excitation of the nerve;
(ii) the transmission of excitation to the muscle fibres and their electrical response;
(iii) the release of ionised calcium into the muscle fibres;
(iv) The sliding interaction of the contractile proteins, actin and myosin within the mechanical element of the muscle fibres; and
(v) an accumulation of molecules formed as intermediates in the chemical reactions of energy release to fuel the mechanical response.

There is strong experimental evidence that an accumulation of these intermediates within the muscle fibres, notably the calcium ion with its action on muscle fibre enzymes (the catalysts of the metabolic and mechanical responses) and other molecular "second messenger" substances are responsible for the induction of structural change in the muscle. It has therefore been necessary to turn attention from the stimuli themselves to the exact time intervals between them.

Figure 3A:
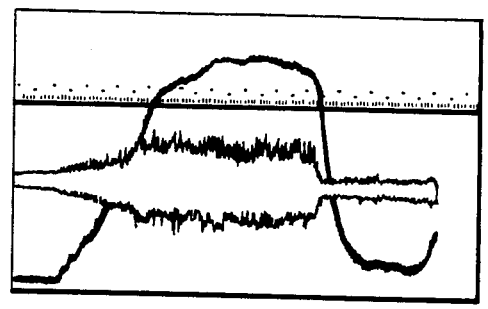
FIGS. 3A-3C and 4A to 4C are oscillograms used in explaining electromyographic techniques.

With classical non-invasive techniques of electromyography identification of individual motor unit action potentials was not possible, and a quantitative description required an integrated electrical signal. The upper trace in FIG. 3A shows a time marker, (10, 50, 100 milliseconds) the middle trace an electromyogram, of human facial muscles and the lower trace, integrated electrical signal of the discharge.

Figure 3B:
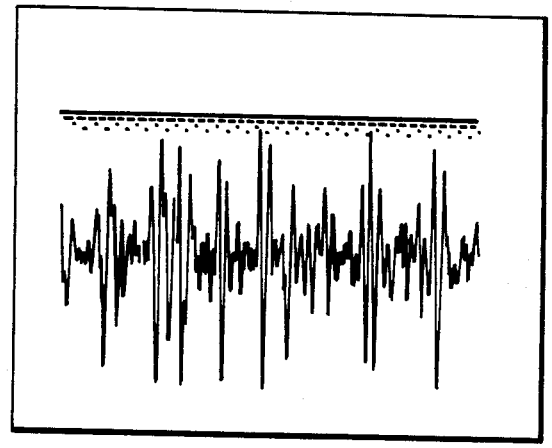
Figure 3C:
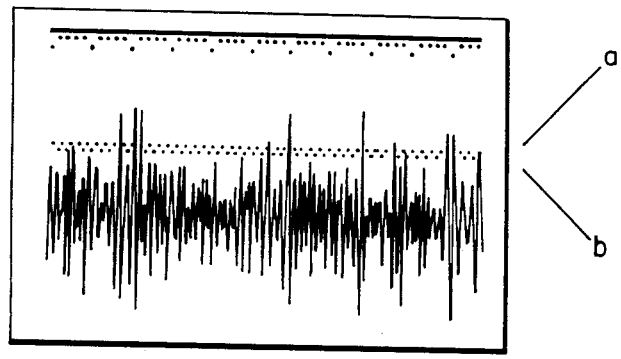

Referring to FIG. 3B, with electromyographic techniques individual potentials are apparent, and their distinct amplitudes make them accessible to detection. Thus, as shown in FIG. 3C, when a potential ends within a detection "window", i.e. between a and b, a signal can be generated which is compatible with a microcomputer and can enter as data into a software program.

Figure 4A:
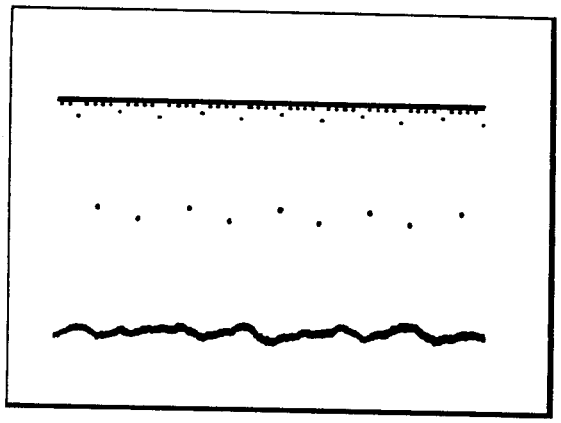

The "window" can be set to a very small voltage. In FIG. 4A it is 12 microvolts. It may be moved through the electromyogram, so dissecting electrically the discharge pattern.

Figure 4B:
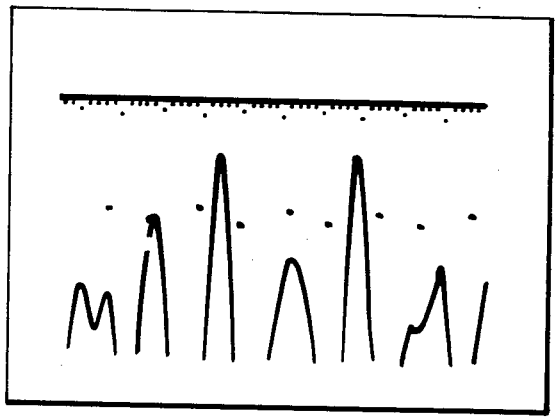
Figure 4C:
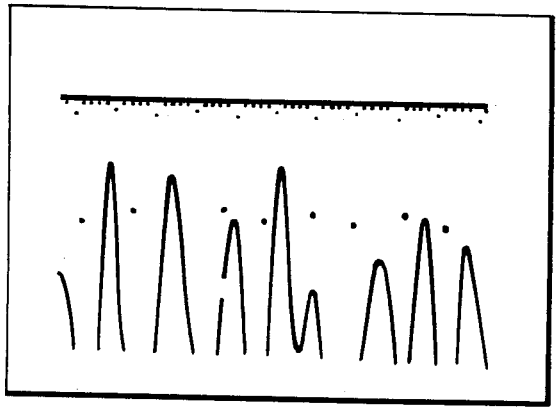

FIGS. 4B and 4C are very high resolution records taken from the facial muscles showing how accurately the motor unit action potential peaks can be isolated and detected.

Figure 5:
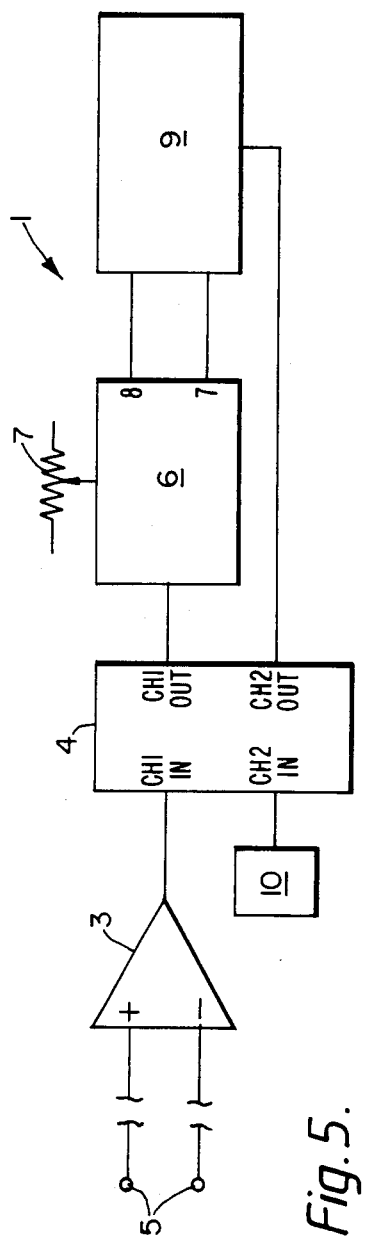
FIG. 5 is a block diagram of one embodiment of electromyographic apparatus.

FIG. 5 shows in block form one version of electromyographic apparatus in accordance with the first aspect of the present invention, which makes use of this technique. The apparatus 1 comprises a sensitive, low noise differential amplifier and filter 3 which is used to amplify the electromyographic signal appearing across two electrodes 5 which may be of the type conventionally used in electromyography. The output of the amplifier 3 is recorded onto one channel of a magnetic tape data recorder 4, a 5 kHz timing marker signal from a reference oscillator 10 being reroded on the other channel. When the tape is replayed, the output of the first channel is applied to the input of a window comparator 6 which compares the instantaneous amplitude of the signal with upper and lower threshold values separated by a sufficiently small voltage (say, 12 microvolts) so that the peaks of only MUAPs associated with one particular motor unit will fall within the comparison window.

The window comparator has two logical outputs, 7 and 8 which change state respectively when the lower and upper window levels are exceeded. These outputs are applied via a suitable interface (not shown) to a suitably programmed microcomputer 9 which also receives the reproduced timing signal so that the timing of the transitions of the outputs 7 and 8 of the window comparator 6 may be established. The window comparator is provided with a user-operable control such as potentiometer 7 allowing the threshold levels at which transitions of the outputs 7 and 8 take place to be shifted, while maintaining the desired difference between these levels. A further control, not shown, may also be provided to adjust the height of the detection window.

In operation, while the window comparator 6 is processing reproduced electromyographic signals from the amplifier 3, the microprocessor monitors the outputs 7 and 8. Each time a positive-going transition of the lower threshold output 7 occurs, the microprocessor 9 stores the current time indicated by the real time clock 10. If and only if the transition of the output 7 is not followed within a defined time period by a positive going transition of the upper threshold output 8, (this condition indicating that the peak of a motor unit action potential fell within the detection window) the read out clock value is stored as relating to a MUAP. Otherwise it is disgarded. The microcomputer 9 can thus record the relative timing of a series of MUAPs associated with an individual motor unit and to calculate both the mean frequency of discharge and the instantaneous frequency, that is the frequency corresponding to the interval between successive discharges. It will be appreciated that in real-time applications, the data recorder 4 is superfluous and the outputs of the amplifier 3 and clock 10 are applied directly to the microcomputer 9.

Standard hardware may be used to implement the apparatus shown in FIG. 5. For example the amplifier/filter 3 may be constituted by Neurolog. NL103 and NL115 units sold by Digitimer Ltd, the data recorder 4 may be of the type DA1442/Q/4/1 sold by Data Aquistion Ltd, the window comparator 6 may be the Digitimer Ltd D130 spike discriminator and detector logic unit and the clock 10 may be constituted by a DI13 A/D converter made by Interactive Structures Inc which can provide an Apple-compatible clock signal.

EXAMPLE

Motor unit action potentials were detected using biopolar skin surface electrodes (Bioscience) attached 5 mm apart on the face. The MUAPs were recorded on magnetic tape, with a remaining tape channel carrying a 5 kHz timing signal. TTL-level compatible pulses generated by single MUAP detections were timed to the nearest millisecond against the 5 kHz clock by an Apple II microcomputer.

Reproducibility of facial movements was obtained by basing them on the test procedures of Kendal and McCreary (Kendal F. P. and McCreary E. K., 1983, "Muscles testing and function", London, Williams & Wilkins). The subjects followed either a repeated video-loop playback of one of their own movements, or a form of visual feedback involving an integrated EMG signal derived from their own MUAP activity. The magnitude of the contractions used was that required to produce an integrated EMG signal between 30% and 35% of the maximum obtainable by the subject. 15 normal subjects with an age range between 20 and 50 were employed in the study, the muscles investigated being Epicranius (Frontalis), Orbicularis oculi, zygomaticus, levator labii and orbicularis oris.

A tonic resting discharge was seen only ocassionally in the muscles studied. Peak MUAP frequencies were recorded in the initial 200 milliseconds of the contractions, between 41 and 30 impulses per second for Orbicularis Oris and from 30 to 25 impulses per second for the other muscles. The mean discharge frequency within single subject (SS) recordings and amongst subjects (AS) were remarkably constant. Calculations from non-fatiguing contractions maintained for between 5 and 10 seconds were:

(SS n=10) Epicranius 8.2+/−1.4 Orb oc. 7.4+/−1.2. Lev. lab. 8.2+/−1.9 Zygom. 7.8+/−1.8 Orb or. 11.7+/−1/1 Lev. lab. 7.1+/−1.4 Zygom. 6.7+/−1.1 Orb.or. 12,8+/0.9

(AS n=15) Epiranius 8.4+/−3.8 Orb oc, 6.9+/−1.1. Lev. lab. 8.2+/−1.9 Zygom. 7.8+/−1.8 Orb pr. 11.7+/−1/1

Table 1 shows a typical result:

TABLE 1

| MOTOR UNIT SPIKE NO. | MOTOR UNIT INTERVAL MS. | ELAPSED TIME MIN | S. | MS. | FREQ. |
|---|---|---|---|---|---|
| 1 | 19 | 0 | 0 | 19 | 52 Hz. |
| 2 | 23 | 0 | 0 | 42 | 43 Hz. |
| 3 | 25 | 0 | 0 | 67 | 40 Hz. |
| 4 | 27 | 0 | 0 | 94 | 37 Hz. |
| 5 | 24 | 0 | 0 | 118 | 41 Hz. |
| 6 | 16 | 0 | 0 | 134 | 62 Hz. |
| 7 | 56 | 0 | 0 | 190 | 17 Hz. |
| 8 | 32 | 0 | 0 | 222 | 31 Hz. |
| 9 | 41 | 0 | 0 | 263 | 24 Hz. |
| 10 | 43 | 0 | 0 | 306 | 23 Hz. |
| 11 | 38 | 0 | 0 | 334 | 26 Hz. |
| 12 | 24 | 0 | 0 | 368 | 41 Hz. |
| 13 | 51 | 0 | 0 | 419 | 19 Hz. |
| 14 | 47 | 0 | 0 | 466 | 21 Hz. |
| 15 | 53 | 0 | 0 | 519 | 18 Hz. |
| 16 | 52 | 0 | 0 | 571 | 19 Hz. |
| 17 | 54 | 0 | 0 | 625 | 18 Hz. |
| 18 | 54 | 0 | 0 | 679 | 18 Hz. |
| 19 | 51 | 0 | 0 | 730 | 19 Hz. |
| 20 | 61 | 0 | 0 | 791 | 16 Hz. |
| 21 | 48 | 0 | 0 | 839 | 20 Hz. |
| 22 | 49 | 0 | 0 | 888 | 20 Hz. |
| 23 | 60 | 0 | 0 | 948 | 16 Hz. |
| 24 | 56 | 0 | 1 | 4 | 17 Hz. |
| 25 | 57 | 0 | 1 | 61 | 17 Hz. |
| 26 | 58 | 0 | 1 | 119 | 17 Hz. |
| 27 | 56 | 0 | 1 | 175 | 17 Hz. |
| 28 | 59 | 0 | 1 | 234 | 16 Hz. |
| 29 | 54 | 0 | 1 | 288 | 18 Hz. |
| 30 | 52 | 0 | 1 | 340 | 19 Hz. |
| 31 | 47 | 0 | 1 | 387 | 21 Hz. |
| 32 | 46 | 0 | 1 | 433 | 21 Hz. |
| 33 | 38 | 0 | 1 | 471 | 26 Hz. |
| 34 | 47 | 0 | 1 | 518 | 21 Hz. |
| 35 | 57 | 0 | 1 | 575 | 17 Hz. |
| 36 | 56 | 0 | 1 | 631 | 17 Hz. |
| 37 | 54 | 0 | 1 | 685 | 18 Hz. |
| 38 | 53 | 0 | 1 | 738 | 18 Hz. |
| 39 | 52 | 0 | 1 | 790 | 19 Hz. |
| 40 | 54 | 0 | 1 | 844 | 18 Hz. |
| 41 | 49 | 0 | 1 | 893 | 20 Hz. |
| 42 | 61 | 0 | 1 | 954 | 16 Hz. |
| 43 | 50 | 0 | 2 | 4 | 20 Hz. |
| 44 | 59 | 0 | 2 | 63 | 16 Hz. |
| 45 | 57 | 0 | 2 | 120 | 17 Hz. |
| 46 | 64 | 0 | 2 | 184 | 15 Hz. |
| 47 | 61 | 0 | 2 | 245 | 16 Hz. |
| 48 | 59 | 0 | 2 | 304 | 16 Hz. |

During a controlled contraction of the facial muscles every discharge spike of a motor unit is detected in sequence (Column 1). It is timed to the nearest millisecond (Column 2). Its relative position in the duration of the activity is computed (Columns 3 and 4) as is the instantaneous frequency of its discharge (Column 5). It is from these computations that the trophic code can be extracted. The following description is based on work carried out using the above techniques.

Skeletal muscle has the ability to adapt its molecular form to better meet functional requirements, that is to say muscle is plastic. It exists in a highly dynamic equilibrium where there is constant breakdown (catabolism) of the molecules which characterise muscular action (e.g. the enzymes associated with the contractile protein myosin, and those which play a role in the energy metabolism). The equilibrium is maintained by biosynthesis of replacement enzyme molecules (anabolism).

In the face of unchanging motor behaviour the equilibrium is simple, the enzymes being replaced unchanged. Motor adaptation however is accompanied by enzyme substitution, where the newly synthesised enzymes show an altered activity more suited to the changing motor demands.

The contact normal nerve makes with normal muscle exerts a "trophic control" on the muscle at rest. The control is unrelated to the impulse traffic transmitted by the nerve to the muscle. Although the definition is now somewhat qualified the action is still within that sphere. Thus neurotrophic action maintains, for example, the integrity and effectiveness of the neuromuscular junction.

To the neurotrophic control is added the effect of impulse traffic over the muscle nerve, and the immediate and eventual effects it has on the metabolism of the muscle fibres. Examples of the degree of influence of the two effects can be seen in a comparison of the considerable wasting or atrophy of a muscle in disuse with the second influence alone missing, with the much more severe denervation atrophy where both are absent. The stability of muscle function, a component of homeostasis, is vigorously defended by body mechanism. Only when evidence of functional incompetence is found does adaptation occur.

Nerve transmits to muscle two simultaneous trains of information:

(i) The first is the command to act mechanically; and
(ii) The second is the command to adapt structurally For the structural adaptation to take place some incompetence signal must be released as a consequence of muscular action. Put in other terms, for adaptation to occur the motor commands to a muscle must subtly mismatch its mechanical capability.

Analysis in the laboratory of the pattern of impulse discharge by the muscle fibres of a motor unit can relate the force it develops and the movement it operates. Any signal detected in the pattern of impulses which is apparently redundant to the immediate motor purpose can be considered to generate an incompetence signal, and can be called the trophic code.

The normal interaction between nerve command and muscular competence naturally regulates plastic change in the muscle fibres. It is hypothesized that where motor abnormality is present due possibly to nervous disease, injury or lesion, the muscle follows its natural tendency for plastic change and becomes better suited to follow the enforced abnormal motor role.

Injection into the muscle by electric stimulation of a difference signal would make good the information deficit by the provision of an artifical trophic code. This procedure we call have called electrotrophic stimulation.

The use of logical detection circuits allow discrimination and timing of the MUAPs generated during movement by normal subjects. From these pattern two contributory patterns can be extracted by computation. One is the dominant represented by the mean discharge frequency, the other is a signal which contributes to that mean but differs significantly from it. This contains the most potent component of the trophic code. It carries the signal CHANGE which comes in the command series:

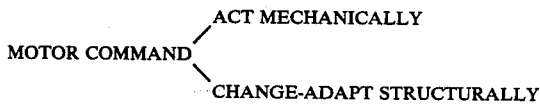

An increasing amount of experimental evidence supports the existence of the trophic code. The time intervals between individual MUAPS and their relation to the time of the muscle mechanical response allow the accumulation within the muscle fibre of specifically potent agents capable of initiating and maintaining metabolic change. Calcium in its ionised form is one example, and the several ionic species in hich adenosine monophosphate exists are others.

Muscular action elicited by low frequency, long duration activity is known to increase the fatigue resistance of muscle, and to induce it to capillarise with blood vessels. Short periods of high frequency bursts of electrical stimulation are less predictable in their action. In the first example the effect of the mean MUAP discharge frequency is having an effect, albeit only partial. In the second, the distinct signal of the trophic code can be seen in only incompletely understood action.

The trophic code cannot at the present time be deciphered, but it can be copied and transcribed.

Taking as a specific example the pattern of discharge of the human facial muscles. (FIGS. 3 & 4). The amplitude of the electrical signal of action in a unit of mechanical response (the motor unit action potential MUAP) is unique. By the employment a series of signals compatible with a computer and timed to the nearest millisecond the trophic code is approximated. Software computer programs have been prepared to transcribe this code as data onto e.g. a PROM I.C.. One such PROM may be provided for each code extracted, or each electrotherapy required by the physiotherapist or orthopaedic clinician.

It is envisaged that a physiotherapist or clinician will be able to prescribe an individual electrotrophic therapy which will be dispensed by in the form of an I.C. or other storage device the appropriate trophic code.

For any form of electrostimulation to be clinically effective it must go beyond the short term, transistory effects and involve the skeletal muscles capacity for a plastic change is enduring and facultative and is represented by the entry of biosynthetic processes (essentially, an incorporation of new proteins not initially present in the muscle fibre), into the metabolic and mechanical pathways of muscular response.

This action involves an expression of genes within the chromosomes of the muscle fibres. Understandably, this unlocking of the genetic potential of a muscle requires a very secure key system. If the response of the muscles is not to be a nonsense or a futile response a subtle code must be available to signal that the change to take place in the muscle will be purposeful and appropriate. This is the trophic code for the muscle.

The discharge that a motor nerve carries into a muscle contains two separate commands which "time share" a common pathway. They are:

(a) the commands which control the generation of force by the muscle as it is;
(b) the command of the trophic code which determines the biochemistry and biomechanics of the muscle as they must become if the muscle's function is to improve.

The response of skeletal muscle to either a naturally discharged nerve impulse or an electric stimulus shows several cyclic responses.

The ion fluxes of the action potential which initiates mechanical action has a cycle time of the order of 1 millisecond.

Calcium ion release from the sarcoplasmic reticulum which couples the bioelectric membrane response to the force generating mechanical response has a cycle time, before it is reabsorbed and sequestered in the sarcoplasmic reticulum once again, of 100 ms.

The "second messenger" release of AMP and its derivatives have an effective life cycle of 1.0s.

Unknown intermediates operate to govern the total protein turnover cycle in muscle which is measured as 120 days.

The cycle time of the agents effective in muscle fibre metabolism give an effective concentration against time relationship illustrated diagrammatically in FIG. 6.

A series of muscle stimuli or natural muscle fibre action potentials, where each successive train shown has twice the frequency of the preceding one, will cause a build up in effective concentration of the cycling agent. (This is indicated by the dotted line increments in effective concentration and the new effect decay curves shown). Putting a real as opposed to a general time scale to the diagram, the likely effectiveness of a pattern of motor unit action potentials (MUAP) in a train can be assessed.

Figure 7:
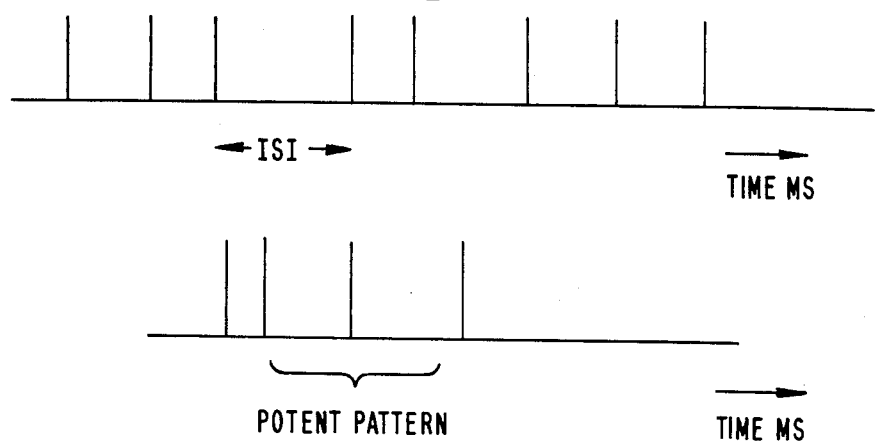
FIG. 7 is a timing diagram showing example interspike (i.s.c.) intervals of muap discharge.

Suppose a discharge pattern of MUAP recorded using the techniques described above in the Example looks as the upper diagram of FIG. 7 the interspike intervals (i.s.i.) having been computed and established as a file accessible to computation. Examination of a series of such patterns may reveal the recurrence of a "potent pattern" such as is shown in the lower plot of FIG. 7. Using the Monte Carlo comparison technique one can seek to identify the trophic information coded onto the pattern.

Consider a computer file containing a time series representing the i.s.i. discharged by a motor unit during such a file can be built up by appending data from a series of measurement runs. Table 2 shows one such run.

TABLE 2

|  | I.S.I. (mS) |
|---|---|
| ELEMENT 1 | 54 |
| ELEMENT 2 | 53 |
| ELEMENT 3 | 54 |
| ELEMENT 4 | 55 |
| ELEMENT 5 | 55 |
| ELEMENT 6 | 59 |
| ELEMENT 7 | 61 |
| ELEMENT 8 | 67 |
| ELEMENT 9 | 73 |
| ELEMENT 10 | 87 |
| ELEMENT 11 | 85 |
| ELEMENT 12 | 103 |
| ELEMENT 13 | 118 |
| ELEMENT 14 | 149 |
| ELEMENT 15 | 173 |
| ELEMENT 16 | 194 |
| ELEMENT 17 | 213 |
| ELEMENT 18 | 215 |
| ELEMENT 19 | 207 |
| ELEMENT 20 | 198 |
| ELEMENT 21 | 199 |
| ELEMENT 22 | 205 |
| ELEMENT 23 | 211 |
| ELEMENT 24 | 219 |
| ELEMENT 25 | 209 |
| ELEMENT 26 | 198 |
| ELEMENT 27 | 198 |
| ELEMENT 28 | 198 |
| ELEMENT 29 | 193 |
| ELEMENT 30 | 195 |
| ELEMENT 31 | 197 |
| ELEMENT 32 | 198 |
| ELEMENT 33 | 197 |
| ELEMENT 34 | 199 |
| ELEMENT 35 | 195 |
| ELEMENT 36 | 200 |
| ELEMENT 37 | 201 |
| ELEMENT 38 | 198 |
| ELEMENT 39 | 203 |
| ELEMENT 40 | 202 |
| ELEMENT 41 | 204 |
| ELEMENT 42 | 200 |
| ELEMENT 43 | 199 |
| ELEMENT 44 | 202 |
| ELEMENT 45 | 203 |
| ELEMENT 46 | 204 |

Figure 8:
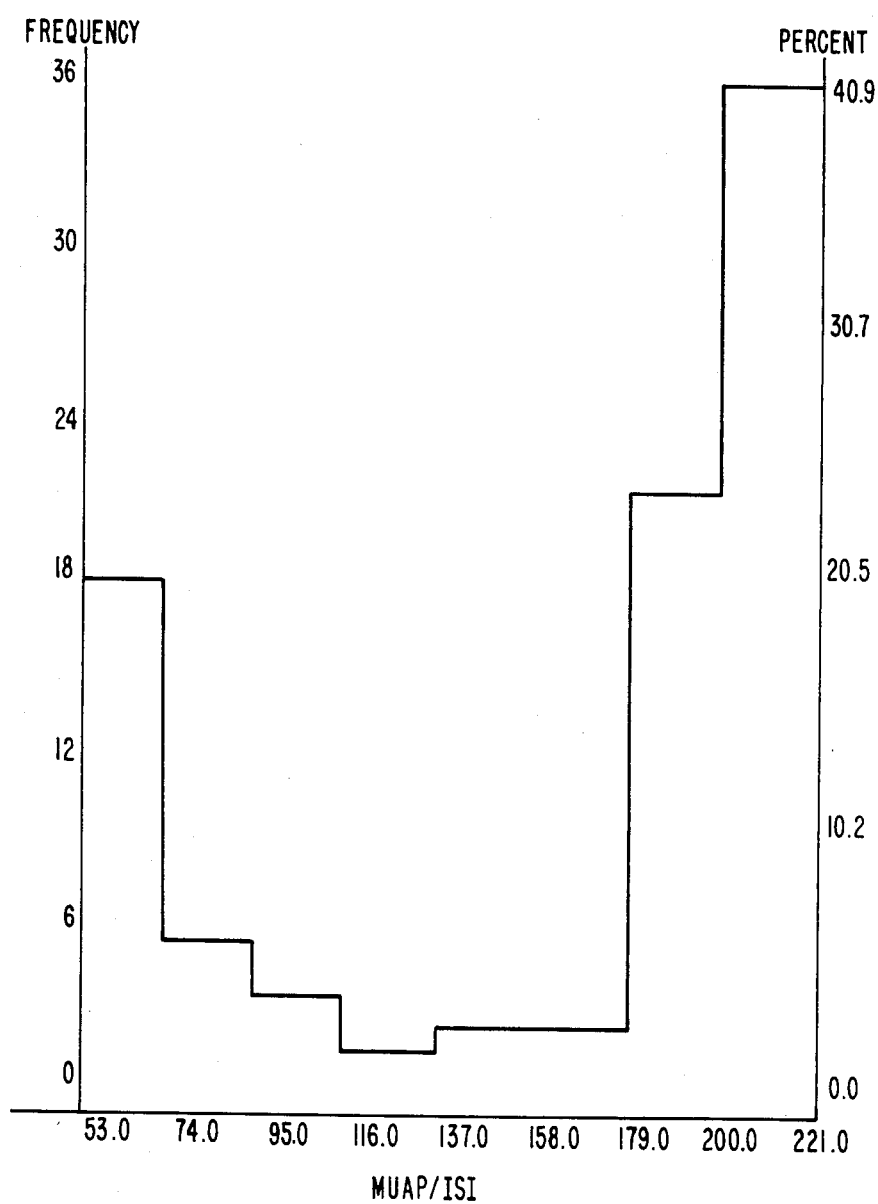
FIG. 8 is a histogram showing frequency of occurrence of various i.s.i. values is a measurement min.

If a sample width of 11 milliseconds is chosen a frequency distribution such as is shown in FIG. 8 may be computed. The frequency of occurrence of i.s.i.s of the values contained in the sample width are drawn.

Non-time series statistical procedural artefacts can be separated from information carrying MUAP discharge trains by randomising or "shuffling" the order of elements in the i.s.i. data file.

Figure 9:
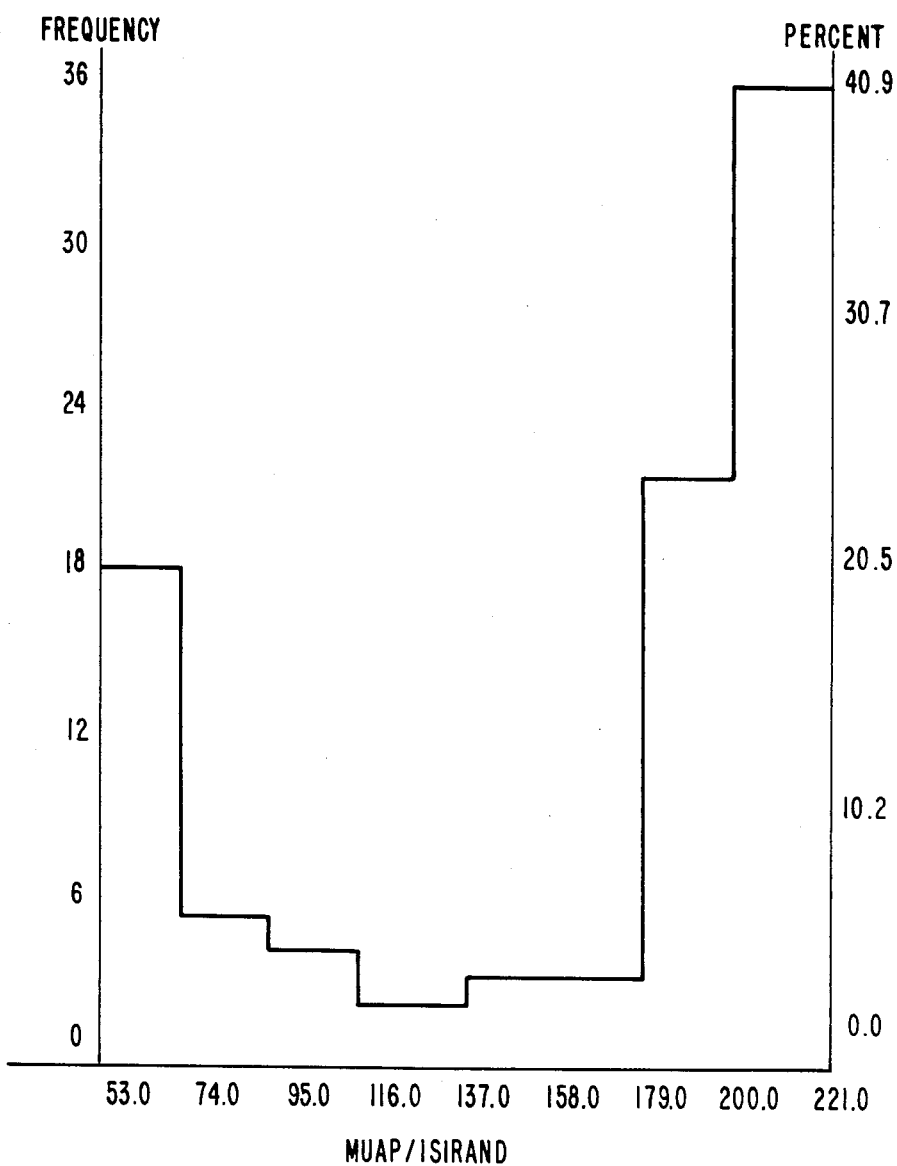
FIG. 9 is a corresponding histogram derived from the same data after random order-shuffling.

A frequency distribution plot of the shuffled data elements is shown in FIG. 9 and shows statistical comparability but the time sequence information has been lost.

The unshuffled i.s.i. data file may be quantized by allocating the value 1 if the isi is between 5 ms, and 10 ms and the value 2 if it is between 5 and 10 ms . . . and so on.

Similarly, the hypothesized "Potent Pattern" may be quantized and a computer search for the number of times it occurs during the time course of the data file a similar search is made of the "shuffled", randomized file for comparison. The digitization process may be carried out using an algorithm such as the following: start interspike interval isi(0) followed by i(1), i(2) . . . i(n).

```
Let x=5 Let t=2
Is x=1- Yes Then STOP
- No
Is i(0)>0 and=<t Yes Then i(0) has the value 1
No
Is i(0)>t and=<2t Yes Then i(0) has the value 2
No
Is i(0)>2t and=<3t Yes Then i(0) has the value 3
No
Is i(n)>(n−1)t and =<nt Yes Then i(n) has the
value n
No
```

Is i(0)>0 and=>t Yes Then i(0) has the value and so on until the series has been digitized with increasing resolution.

Suppose a suspected potent pattern comprises the sequence of i.s.i.s 2, 1, 3, 1. Then a search through the digitized unshuffled data file can be carried out to establish its frequency of occurrence; a similar search through the digitized shuffled file, will help identify whether the pattern is a significant time-series pattern.

The occurrence of a "potent pattern" could be sought by computation amongst the patterns generated:
(i) during constant movement in normal muscle.
(ii) during movements requiring muscular adaptation for their performance.
(iii) during movements performed by muscles rehabilitating to movement after injury or disease.

The effectiveness of the technique in establishing the "trophic code" may be increased by making the stages of MUAP detection, measurement and quantization at times when induced adaptation of normal muscle is occurring.

In an accustomed movement to which a muscle is adapted there is a definable relationship between the force it develops and the way in which that force is developed.

Figure 10:
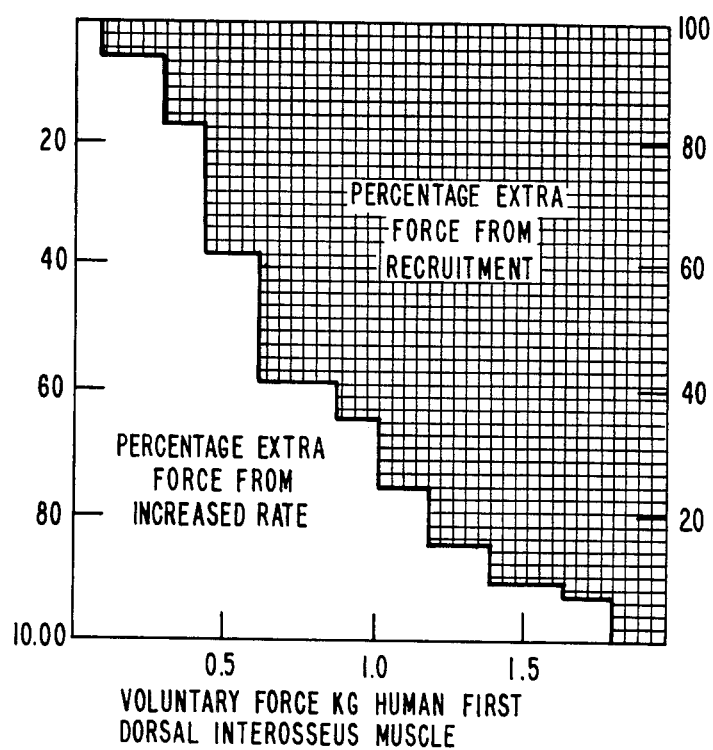
FIG. 10 illustrates the behaviour of muscle for various exerted forces.

Motor units can be recruited to action, each contributing its available force, and the available force can be amplified by increasing the rate at which the motor unit is excited and generates its force. FIG. 10 illustrates this relationship for a hand muscle. As this represents the "signature" of the muscle in normal action and deviation from it during abnormality or rehabilitation reveals a factor involving the frequency of discharge of discharge with respect to recruitment and force development that refines the procedures of reasoning, analysis and computation described above.

Analyses based on the calculations just described have yielded, as an example, one trophic code in which the i.s.i.s show an initial value of 22 ms, indicating a discharge frequency of approximately 50 Hz. This i.s.i. increases in an exponential fashion and the discharge rate slows to 5 Hz.

Where the number of MUAPs is large, or where the larger limb muscles are being studied, the above described window detection can be supplemented by the use of a single detector beam which is stepped, by regular decrements in detection voltage, down through the signal. Computer files can then be established of the time intervals between the compound MUAP potentials detected each level, and software can then establish the code for the individual motor units by a subtraction routine operating on each of the files in turn; this can take into account the possibility of interference signals from the larger number of potentials.

Figure 11A:
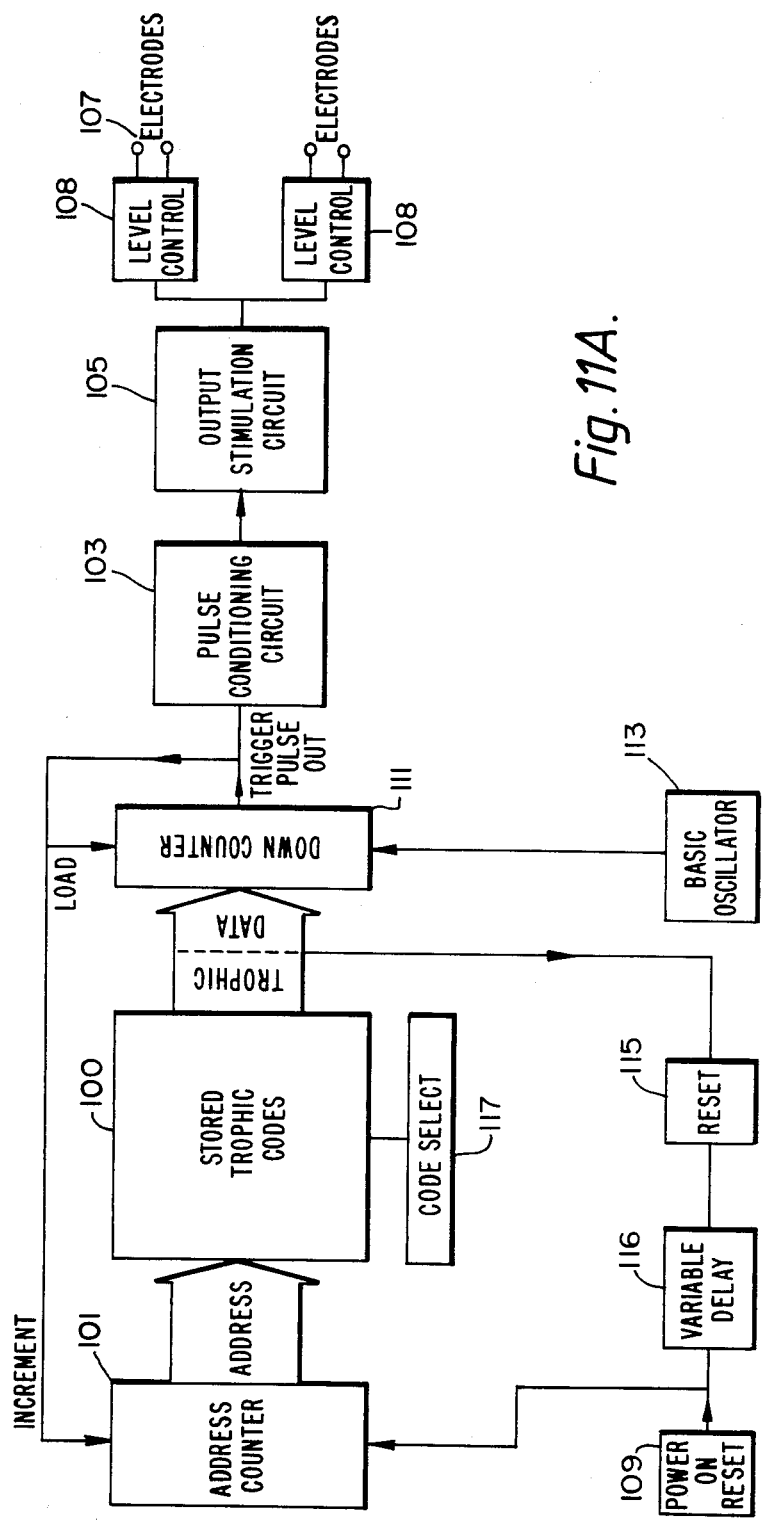
FIG. 11A is a block diagram of one embodiment of muscle stimulating apparatus according to the present invention.

FIG. 11A shows one form of muscle stimulating apparatus according to the present invention. A memory device 100, which may be in the form a PROM (programmable read only memory) integrated circuit has stored therein data defining a pulse sequence on which is coded trophic information with which it is desired to stimulate a muscle or muscle group. This information is coded as the respective time intervals between successive pulses which are to be generated. This data is sequentially read out, and, in a manner to be described in more detail below, used to generate a train of fixed length pulses. The relative timing of the pulses, i.e. the intervals between successive pulses conveys the desired trophic information. This pulse train is applied to one or more output channels comprising a pulse conditioning circuit 103 which may, inter alia, buffer the signal produced and/or modulate the pulse waveform into a succession of bursts with spaces therebetween; the bursts may have a shaped envelope. The output of pulse conditioning circuit 103 is applied to an output stimulation circuit 105 which may incorporate a step up transformer and/or level control circuitry to transform the signal to the appropriate level for muscle stimulation and/or to define a desired source impedence for the stimulating signal. This stimulating signal is applied to two or more output electrodes 107 which are placed in contact with the skin overlying the muscle or muscle group of interest. Where there are more than two output electrodes, individual electrodes may have individual level controls such as the potentiometer 108 shown in FIG. 13.

The memory 100 may be paged, having a number of trophic codes which may be of different lengths, and in these circumstances a code selector 117 (e.g. a multiposition switch may be used to select the code to be generated).

At the start of operation, a power-on reset circuit 109 generates a pulse which is applied to the "clear" input of address counter 101. The address counter 101 generates an address signal which is applied to the memory 100 causing the contents of its first storage location on the selected page, representing a first pulse interval, to read out as data. This read-out data is applied to the "load" input of a down-counter 111 whose stored count then proceeds to be decremented by the application of clock pulses from an oscillator 113 having a frequency of, say, 1 KHz. This gives a minimum interval of 1 mS. In this unit the interval between trophic code pulses is an integral number of milliseconds. Should higher resolution be necessary a higher frequency could be used;

When the count stored by the down-counter 111 reaches zero, a pulse is produced at its "zero" output, lasting the duration of one clock pulse from the oscillator 113. This pulse is applied both to the pulse conditioning circuit 103 for conditioning and application to the electrodes 107 and to the "increment" input of the address counter 101 causing the timing data in the next storage location in the memory 100 to be read out.

The "zero" pulse from the down-counter 111 also causes this read-out data to be loaded into the down counter 111, whose contents thereupon proceed to be decremented by the pulses from oscillator 113 resulting, after a time period defined by the value of the read-out data word in the application of a further pulse to the pulse conditioning circuit 103. This process repeats for each of the items of data stored in the memory 100.

As the number of data words required to produce the desired pulse sequence may be less than the available contents of the memory, the desired sequence may be terminated by a pre-defined word value e.g. 000 .... A reset circuit 115 may be provided to detect the occurrence of this terminating word and apply a pulse to the "clear" input of the address counter 101 so that generation of the required pulse sequence recommences at that point.

A variable delay block 116 may be provided to allow for an adjustable delay between successive generating cycles of the stored code. This can enable the pulses to be produced in spaced apart bursts.

It will thus be appreciated that the stimulator 100 operates to generate a sequence of fixed length pulses, for application to the muscle/muscle group or overlying tissue, with intervals between successive pulses determined by the values of successive data words stored in memory 100. By appropriate selection of these intervals, the desired trophic information can be coded onto the pulse sequence applied via the electrodes 107 to produce a particular long term adaptation of the muscle/muscle group in question.

The memory device 100 may be of any suitable form; conveniently it is a PROM (programmable read only memory) IC although any other suitable device such as a magnetic or optical disc, tape, RAM IC, bubble memory, shift register and so forth may be used - even a series of switches which can be set to one of a number of positions to define respective pulse intervals. In any event, conveniently, the device may be such that the data read out can readily be changed so that trophic data for a variety of treatments can be used on a single stimulator 100 as selection of a different code stored in the memory 100, using the selector 117 or by user replacement of one PROM conveying particular trophic data by another. It is also possible, using a suitable read/write memory for the required data to be down loaded from a remote source e.g. via modem, local area network or any other suitable communications link, thereby enabling "treatment at a distance".

The pulse conditioning circuit and the output stimulation circuit may be so designed to maximize the subcutaneous response but minimize the response of peripheral pain receptors. Thus prolonged application of stimuli should present no difficulty.

The design of the output stimulation circuit is such that it basically acts as a very low impedence current source yet will limit the surface voltage should the load impedence increase excessively. This aspect of the design therefore prevents "biting" or "stinging" from electrodes being removed or repositioned during treatment. The pulse width and envelope shape are determined by the pulse-conditioning circuit and are selected so that current pulse rise-time, current pulse amplitude and current pulse-width provide maximum subcutaneous stimulation but avoid affecting the peripheral pain receptors. The exact values of these parameters depend on the size and charcteristics of the muscles being addressed. For example on small twitch muscle such as facial, the pulse-width parameter is usually set at approximately 80 uS whereas for a larger muscle group (Quads) a pulse-width of 200 uS may be used.

Figure 11B:
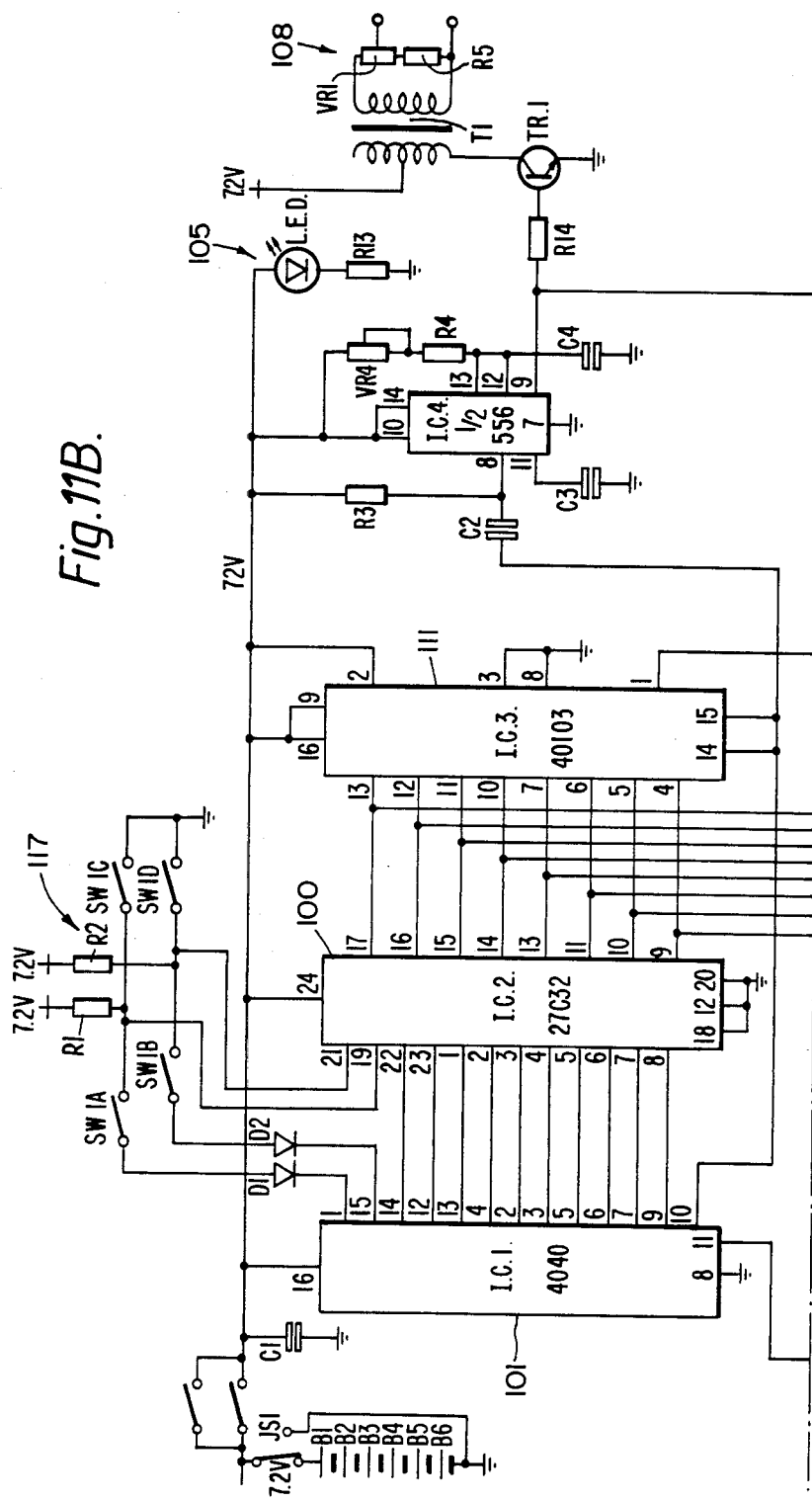
FIG. 11B is a circuit diagram of the embodiment shown in block form in FIG. 11A.

FIG. 11B is a circuit diageram showing one particular form the embodiment of FIG. 11A may take. The following components may be used in the circuit of FIG. 11B:

| | |
|---|---|
| IC1 | 4040B CMOS down counter |

| | -continued |
|---|---|
| IC2 | 27C32 PROM |
| IC3 | 40103 CMOS down counter |
| IC4 | 556 Dual timer I.C. |
| IC5 | 4532 CMOS priority select/encoder |
| IC6 | 4096 CMOS quad schmidt trigger |
| TR1,TR2 | BDX 53B |
| $R_1,R2$ | 100K |
| R3,R10 | 10K |
| R4,R6 | 2K2 |
| R5,R7 | 470R |
| R8,R9 | 51K |
| R11 | 500K |
| R12 | 470K |
| R13 | 820R |
| VR1,2,4 | 2K2 preset |
| VR3 | 470K preset |
| C1 | 1000 uF |
| C2,C7 | 1000 pF |
| C3,C5,C6 | 0.01 uF |
| C4 | 0.022 uF |
| C8 | 10 uF |

In FIG. 11B, the reference numerals 100–117 indicate the correspondencies between the circuitry shown in FIG. 11B and the circuit blocks in FIG. 11A and further description of FIG. 11B is not therefore considered necessary.

Figure 11B:
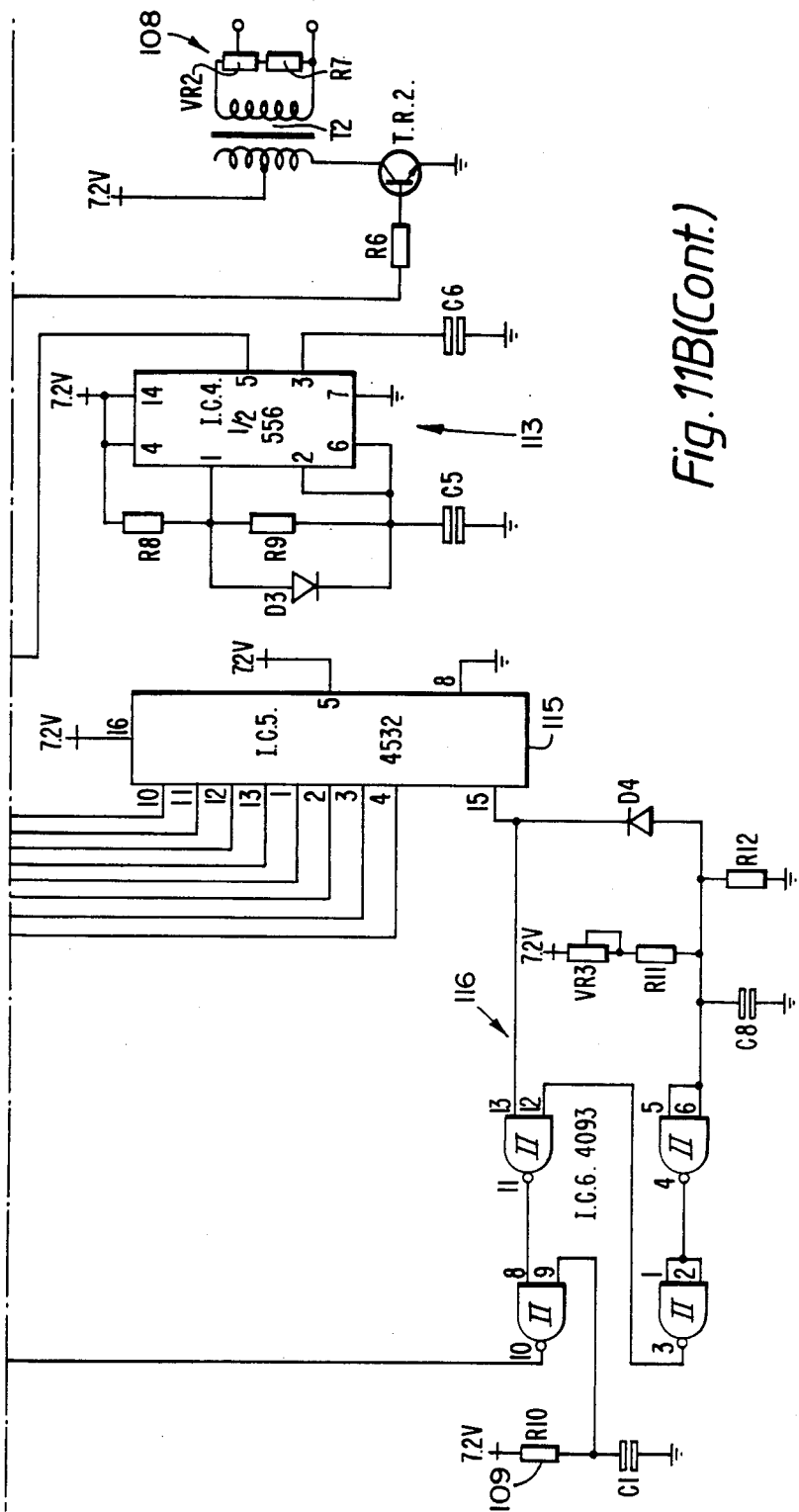

It will be appreciated that the circuitry shown in FIG. 11 is one of many circuits which may be used to translate the stored data into the desired pulse train. For example, the pulse generation could be achieved in software by a suitably programmed microprocessor reading the data defining the desired pulse sequence from a memory device such as a PROM or any of the others mentioned above, the microprocessor delivering from a suitable output a train of pulses for conditioning as by the circuits 103, 105 and application to the electrodes. It is also envisaged that patients could be issued with a machine-readable treatment card on which is recorded, or at least identified, the trophic data to be used for treatment; this card could also have in machine readable form details of the patients, the condition which is to be treated and so forth.

The pulse conditioning circuit and the output stimulation circuit may be so designed to maximize the subcutaneous response but minimize the response of peripheral pain receptors. Thus prolonged application of stimuli should present no difficulty.

A further possibility is that the code generator unit may store within the code memory values to alter the stimulation pulse-width, stimulation pulse-amplitude, stimulation pulse rise and fall times. Thus a more elaborate development may totally describe numerically a stimulation pulse itself and the time interval to the next pulse.

It should be possible by feedback to adaptively and dynamically in real-time modify a trophic code being applied to a patient.

This would necessitates a sensor element (possibly electromyographic) feeding information to a processing unit (microcomputer) programmed with appropriate digital filtering and signal processing algorithms, based on physiological parameters inputs which could adaptively alter the trophic code sequence to converge on a predefined physiological goal.

Figure 12:
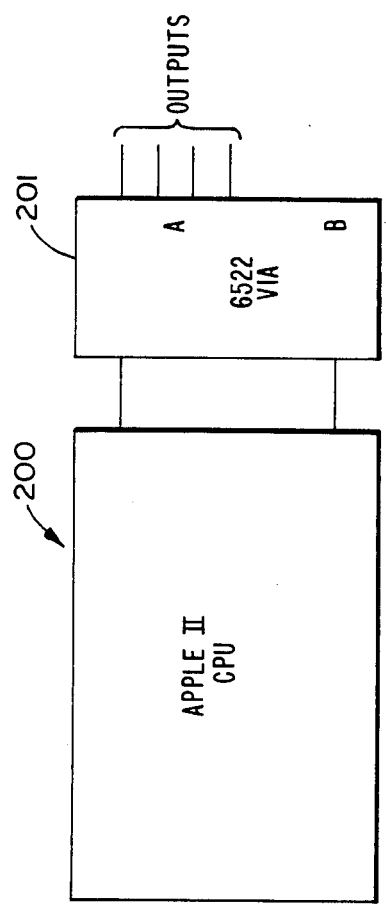
FIG. 12 is a block diagram of a second embodiment of muscle stimulating apparatus according to the present invention.
Figure 14A:
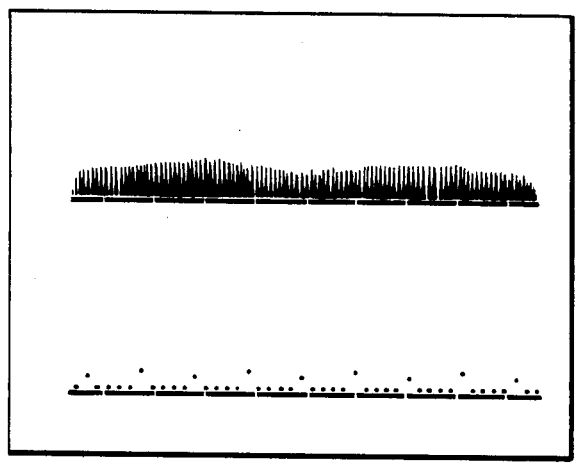
FIGS. 14A and 14B show waveforms of stimulating pulses applied using the embodiment of FIG. 9.
Figure 14B:
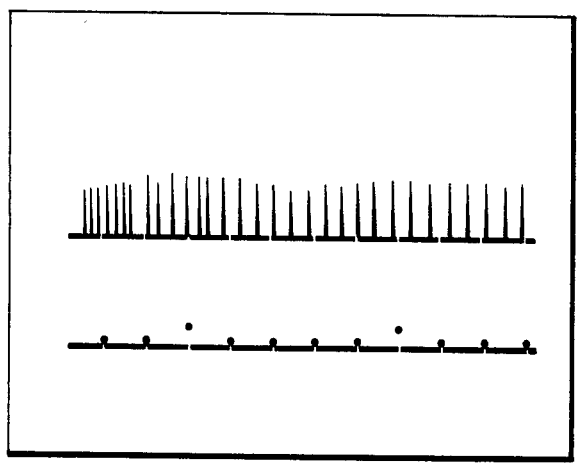

A second embodiment of the invention, shown in FIG. 12 uses Apple II microcomputer 200 incorporating an output device in the form of a 6522 VIA (versatile interface adaptor) 201 installed in an option slot to output stimulating pulses as exemplified in FIGS. 14A and 14B.

Both sides of the VIA are used for output, with positive going signals on the A-side output and negative going signals on the B side output. The A-side positive going pulses have been provided in case external amplification (and resulting signal inversion) are necessary.

The TIMER1 of the VIA is used to synchronise the system and is set to a count of 2048 pulses, this with the Apple's clock speed of 1.024 MHz. gives a synchronisation every 2 msec. In this interval software to be described below can service each of the eight channels, decrement a count, output a pulse (if required) and fetch the next count from memory. The time taken to do this is of the order of 1 msec if no pulses are required on that particular cycle. The worst case occurs when all channels require a pulse. The time to service this condition increases to 3 msec. In this case the software will resynch as long as the delay to then next pulse is more than 4 msec.

The software is not interrupt driven and interrupts are disabled. The synch mechanism just waits in a software loop until the timer has counted down to zero.

The software has been developed for the Apple II computer in 6502 assembler, and these routines interface to the UCSD Pascal system of the Apple. This has facilitated the development of software for data entry and encoding of the files containing the profiles of the pulse sequences. One version of the software is shown in FIG. 13.

The output from the Apple will drive eight channels to an accuracy of 2 msec with a sequence of up to 63 pulses per channel.

There are three patient protection features within the routines which will either cause premature termination of the program or inhibit the output. These features will come into play if the pulse sequences are incorrectly coded or in the event of a hardware fault resulting in spurious data being read. Each data word for the pulse routine has four attributes. These are a count, an encoded channel number, if a pulse is required (on the count ultimately reaching zero) and finally if the channel is on. The conditions required to output a pulse on a given channel are:

1. The count has reached zero
2. The current channel number matches the encoded channel
3. A pulse is required
4. The channel is on.

There are two routines written in assembler. The first, SETVIA sets up the VIA device for outputs on both the A- and B- sides. The A- side is initialised to zero volts (for +ve pulses) and the B- side is initialised high (between 4 and 5 volt TTL) for negative going pulses. This routine also sets the TIMER1 of the VIA in a free running mode to generate the synchronisation signal of 2 msec. Interrupts are disabled.

The second routine PULSES services data from a file containing the encoded pulse trains. The encoded data is treated as if it were ROM and no attempt is made to modify it from within the PULSES routine.

The PULSES routine uses PAGE ZERO locations of the Apple to maintain the counts required to output on each channel. On entry the current contents of PAGE ZERO are saved (to be restored on exit from the routine). The routine maintains a table of pointers into the ROM and also a table of values of the current counts for each channel.

The PULSES routine then services each channel in turn, decrementing the current count. If the count becomes zero then a pulse is output on the current channel only if the following conditions are met:

The channel encoded in ROM data matches the current channel;

The current channel is on; and

A pulse is required.

If the first of these condition fails an error code is generated and the PULSES routine make an abnormal exit.

If the channel is on and the channel has been verified then the next count is brought down from ROM.

The routine can be regarded as follows:

```
error : = 0 ;
while (any_channels_on) and (error<>0) do
begin
    for chan := 7 downto 0 do
    begin
        if channel_is_on [chan] then
        begin
            decrement_count [chan] ;
            if count = 0 then
            begin
                if chan<>codedchan then
                error:=1+256*chan ;
                else
                begin
                    if pulse_required then pulse [chan ] ;
                    get_next_count_from_rom ;
                end;
            end
        end
    end
end;
```

The 16 bit words in the ROM file are encoded with the following information:

| bits 0 ... 9 | the count |
| bits 10 ... 12 | the channel number |
| bit 13 | for future expansion |
| bit 14 | set to 1 if pulse required |
| bit 15 | set to 0 if channel is on. |

With this configuration if the data word is in error as 00 or FF then no output will result. This is because 00 will have bit 14=0 and no pulse will be required, FF will have bit 15=1 and the channel will be off. (This of course assumes test the test for channel quality was successful).

Encode operates on a text file (created with the system editor) to produce a file of encoded ROM data.

The Pascal program ENCODE sets up the data files in the correct format for the PULSES machine code pulse generator routine.

An example of the input data file is as follows:

Set channel 0 with delays 10 20 30 40 msec channel 1 with an initial delay of 50 msec (with ref to the start of channel 0) and then 40 30 20 10 5 msec channel 4 with delay of 100 50 20 20 5 7 8 9 10 11 12 13 14 15

The data file is as follows

| 0 | 1 | 10 | 20 | 30 | 40 | −1 | −1 | −1 |
| 1 | 50 | 40 | 30 | 20 | 10 | 5 | −1 | −1 |
| 4 | 100 | 50 | 20 | 20 | 5 | 7 | 8 | 9 |
| 4 | 10 | 11 | 12 | 13 | 14 | 15 | −1 | −1 |

NOTE

1) The initial 1 in channel 0's sequence to set a reference for subsequent delays.
2) The resolution required in channel 4 is too stringent and the sequence ultimately output by the machine code routine will have a resolution of 2 msec. The actual output for this channel would be 100 50 20 20 6 8 8 10 10 12 12 14 14 16.

The above described stimulator has been used in relation to Bell's palsy. The stimulation pattern consists of stimulation/relaxation cycles (1.45 on/1.45 off) at between 5 and 8 Hz (stimuli per second), this being the frequency of firing adopted by normal facial muscles.

One development of the basic concept of trophic stimulation is that of summation stimulation.

Adequate stimulation of mechanoceptors in muscle, with vibration for example, can be made to summate in effectiveness with electrical stimulation at a level subthreshold for independent excitation. The summation of the two forms of stimulation will be potent in generating reflex action in the spinal cord.

The resulting reflex effect, the inhibition of spastic hypertonus for example, can be detected electromyographically from the surface of the affected muscles, the processed signal from that detection will interact with the computer controlling the two forms of stimulation, trophic and functional, to optimise both frequency and amplitude of the summating electrical and mechanical stimuli.

Trophic stimulation, as described above conditions the muscle's blood supply, its metabolism and the mechanical action to which the energetics of metabolism is applied.

As mentioned above, electrotrophic stimulation may be combined with functional stimulation to achieve a desired psyiological goal.

With functional stimulation the object is to make a muscle, no longer under voluntary control, cause it to contract artificially at a time in synchronism with either whatever natural control is available or with some computed pattern of stimulation applied to other muscles. This is, of course, in itself well known and studied.

Trophic stimulation on the other hand, is new, and when based on computations of the natural discharge patterns of motor units in the muscles involved, is termed eutrophic stimulation.

A muscle that has been in disuse for some time, due to denervation, to total or partial paralysis, to immobilisation or injury, atrophies. A careful analysis of the condition of the muscle shows a reduction in the number of blood capillaries providing oxygen and nutrients for action, and the opportunity for eliminating from the muscle the metabolic products of that action and of work. There is loss of muscle protein, and an alteration in the connective tissue component of the organ.

The muscle therefore becomes unfitted to work. When to this disability, the extreme susceptibility of the muscle fibres to degenerative influences, which include the act of electrical stimulation and artifical muscle action so enforced, is added, it is apparent that ill-considered functional stimulation can be a self defeating procedure.

Eutrophic stimulation by comparison, is calculated first to improve the muscle vascularisation without involving the muscle in self destructive activity. Simultaneously it improves the protein mass of the muscle and its effectiveness during muscular activity. It also reduces the susceptibility of the muscle to self-induced degeneration.

The characteristics of stimuli needed in functional stimulation are set not by the natural firing frequency of motor units in the spinal cord, but by the need for an unnatural excitation lacking the subtelty of normal central nervous system control, designed to compel the muscle to apply force to the joints.

At present state of development of eutrophic stimulation it is apparent that the stimulation trains and patterns must occupy a much longer time than do those of the functional stimulus. Eutrophic stimulation can therfore be used to equip the muscle, in terms of its vascularisation, its dependent metabolism and mechanical action, to act in response to and tolerate indefinitely the functional component of stimulation.

Figure 15:
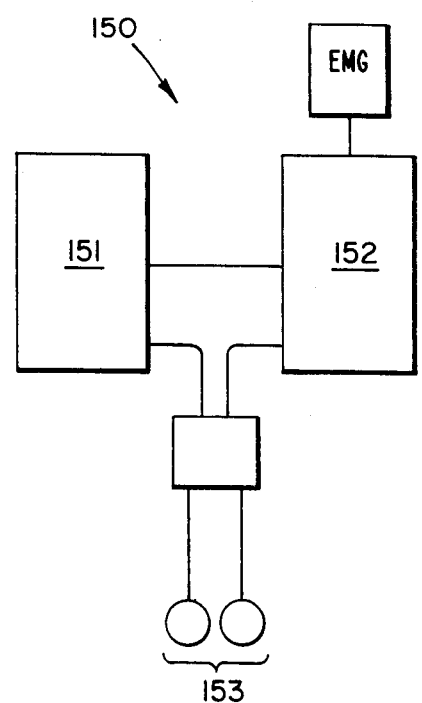
FIG. 15 shows a form of combined electrophic and functional stimulator according to the present invention.

FIG. 15 shows an embodiment of the invention for implementing a combined electrotrophic and functional stimulation procedure. The stimulator 151 comprises 3-channel electrotrophic stimulator 151, which may be in accordance with any of the above-described (or indeed, ay other) embodiments of the invention, a functional stimulator 152 and a set of stimulation electrodes 153 to which the output of one or other of the stimulators 151 and 152 is applied.

The currently available stimulators can now be modified to mix both characteristics of stimulus and have them converge in effectiveness onto one electrode pair.

The stimulator has two distinct stimulation modes. In the first, the three channels of the electrotrophic stimulator 151 will deliver separately eutrophic patterns of stimulation. These will be patient operated in that they can start and end the procedure of pattern stimulation. The repetition of patterns, with, say, two seconds on and two seconds off will probably have to last for at least six hours continuously a day. The three channels deliver to the muscle three evolving therapies to be changed during the first three months of use under the supervision of a clinician of physiotherapist. The conditioning of the muscle for functional stimulation will in this way be optimised.

The second major mode of stimulation is functional and provided by the stimulator 152. The determination of timing and stimulus characteristics will depend on patient physique and disability, and upon what muscle function it is desirable to restore. As shown, the functional stimulator may be programmed by the output of an EMG device and by user input by the clinician. Suitable hardware and/or software is provided to give the required programmability. The functional stimulator may exert an inhibitory control over the electrotrophic stimulator, or the stimulator oututs may be otherwise arranged, so that the functional and trophic stimulators are not applied at the same time.

The programmability of the stimulator will facilitate the tuning of the stimulator in the clinic. It will also make easy the re-tuning that will be required as the muscle adapts to use under stimulation conditions.

The stimulator may be arranged so that functional stimulation is controlled intrinsically, in a manner tuned initially by the clinician, and eventually later in the treatment the functional stimulation is controlled by detection of EMG potentials or their integrated signal detected in muscles still functioning.

We claim:

1. Apparatus for the stimulation of muscle fibre by the application of a stimulating electrical signal to the muscle fibre or to overlying tissue, comprising control means, pulse generating means for generating an electrical signal for use as said stimulating electrical signals and whose waveform carries information which affects the response of said muscle fibre to its stimulation by said signal and at least one pair of electrodes to be placed, in use, in electrical contact with the muscle fibre or overlying tissue, the pulse generating means being responsive in use to the control means to generate as said stimulating electrical signal a sequence of electrical pulses whose characteristics code for electrotrophic information thereby to convey electrotrophic information to the muscle fibre to bring about an electrotrophic response in said muscle fibre for effecting change in the muscle fibre to cause desired structural and/or functional adaptation of the muscle, and to supply the sequence of electrical pulses so generated to the said at least one pair of electrodes, which electrodes transmit the sequence of electrical pulses supplied by the pulse generating means to the muscle fibre or overlying tissue to impart thereto the electrotrophic stimulation to effect the desired structural and/or functional adaptation of the muscle.

2. Apparatus according to claim 1 wherein the pulse generating means includes means for storing electrotrophic data relating to one or more specific muscles or muscle groups and for generating said sequence of pulses in accordance with said data.

3. Apparatus according to claim 2 wherein the pulse generating means further comprises translation means for translating the stored data into at least one-characteristic of the pulse signal which conveys electrotrophic information.

4. Apparatus according to claim 3 wherein the translation means comprising timing control means for translating the electrotrophic data into timing characteristics of the pulse sequence.

5. Apparatus according to claim 4 wherein the timing control means include means for setting the mark and/or space durations of successive pulses.

6. Apparatus according to claim 3 wherein the storing means comprises a number of addressable storage locations, each for storing respective time period values, the pulse generating means including means for successively reading the stored time period values and for generating pulses whose mark and/or space periods are defined by the timing period information.

7. Apparatus according to claim 3 wherein the pulse generator includes means for producing the pulses in bursts.

8. Apparatus for the stimulation of muscle fibre by the application of a stimulating electrical signal to the muscle fibre or to overlying tissue, comprising control means, pulse generating means for generating an electrical signal for use as stimulating electrical signals and whose waveform carries information which affects the response of said muscle fibre to its stimulation by said signal and at least one pair of electrodes to be placed, in use, in electrical contact with the muscle fibre or overlying tissue, the control means selectively controlling, in use, the pulse generating means to generate as said stimulating electrical signal a sequence of electrical pulses whose charateristics code electrophic information thereby to convey electrotrophic information to the muscle fibre to bring about an electrotrophic response in said muscle fibre for effecting change in the muscle fibre to cause desired structural and/or functional adaptation of the muscle, or a sequence of electrical pulses whose characteristics code Faradic information to convey Faradic information to the muscle fibre to bring about a Faradic response in said muscle fibre and to supply the sequence of electrical pulses so generated and coding the stimulating information to the said at least one pair of electrodes, which electrodes transmit the sequence of electrical pulses supplied by the pulse generating means to the muscle fibre or overlying tissue to effect the desired structural and/or functional adaption of the muscle or the Faradic stimulation respectively.

9. Apparatus according to claim 8 and including electrotrophic pulse generating means and functional stimulation pulse generating means, and means for selectively supplying either the electrotrophic pulse sequence or the functional stimulation pulses to the electrodes. and means for selectively supplying either the electrotrophic pulse sequence or the functional stimulation pulses to the electrodes.

10. Apparatus according to claim 8 and including means for establishing the functional stimulation to be produced by the functional stimulation pulses.

11. Apparatus according to claim 10, wherein the establishing means includes electromyographic means for examining functional stimulation pulses naturally produced by a person's nerve fibres.

12. Apparatus according to claim 8 wherein the pulse generating means includes means for storing electrotrophic data relating to one or more specific muscles or muscle groups and for generating said sequence of pulses in accordance with said data.

13. Apparatus according to claim 12 wherein the pulse generating means includes translation means to translate the stored data into at least one characteristic of the pulse signal which conveys electrotrophic information.

14. Apparatus according to claim 13 wherein the translation means comprise timing control means to translate the electrotrophic data into timing characteristics of the pulse sequence.

15. Apparatus according to claim 14 wherein the timing control means include means to set the mark and/or space durations of successive pulses.

16. Apparatus according to claim 12 wherein the storage means comprises a number of addressable storage locations, each for storing respective time period values, the pulse generating means including means for successively reading the stored time period values and for generating pulses whose mark and/or space periods are defined by the timing period information.

17. Apparatus according to claim 12 wherein the pulse generator includes means for producing the pulses in bursts.

18. Apparatus according to claim 16 wherein the pulse generator includes means for producing the pulses in bursts.

19. A method of applying stimulating pulses to muscle fibre comprising generating and applying to the muscle fibres, or to overlying tissue, a stimulus pulse sequence, the pulse sequence being so selected that its waveform carries information which affects the response of said muscle fibre to its stimulation by said stimulating pulse sequence and its characteristics convey electrotrophic information to the muscle fibre for causing a desired structural and/or functional adaptation of muscle fibre of which a muscle is comprised and applying said sequence of pulses to the muscle, or to overlying tissue whereby an electrotrophic response is brought about in said muscle fibre to effect the desired structural and/or functional adaptation.

20. A method according to claim 19 and including the step of storing electrotrophic data relating to one or more specific muscles or muscle groups, reading out such data relating to a particular muscle or muscle group and generating said sequence of pulses in accordance with the read-out data.

21. A method according to claim 20 and including the step of translating the stored data into at least one characteristic of the pulse signal which conveys electrotrophic information.

22. A method according to claim 21 wherein the electrotrophic data is translated into timing characteristics of the pulse sequence.

23. A method according to claim 22 wherein the timing characteristics include the mark and/or space durations of successive pulses.

24. A method according to claim 20 wherein the storing step comprises for storing respective time period values for successive pulses to be generated in a number of addressable storage locations, the time period values of defining the mark and/or space periods of successive pulses.

25. A method of applying stimulating pulses to muscle fibre comprising the steps of generating and applying to the muscle fibres, or to overlying tissue, two or more stimulus pulse sequences, a first one of the pulse sequence being so selected that the pulse sequence conveys electrotrophic information for causing a desired structural and/or functional adaptation of muscle fibre of which a muscle is comprised and applying said sequence of pulses to the muscle, or to overlying tissue and a second one of the pulse sequences being so selected as to cause a desired faradic stimulation of the muscle fibre.

26. A method according to claim 25 wherein the step of applying the two or more pulse sequences comprises applying the first and second sequences of pulses in a treatment sequence to regenerate the muscle and/or improving its mechanical performance.

27. A method according to claim 26 wherein the treatment sequence comprises applying the first and second pulse sequences a multiplicity of times, and varying, during the treatment sequence, the relative frequencies of application of the first and second pulse sequences.

28. A method according to claim 25 and including the step of storing electrotrophic and functional stimulation data relating to one or more specific muscles or muscle groups, reading out such data relating to a particular muscle or muscle group and generating said sequence of pulses in accordance with the read-out data.

29. A method according to claim 28 and including the step of translating the stored data into at least one characteristic of the pulse signal which conveys electrotrophic information.

30. A method according to claim 29 wherein the electrotrophic data is translated into timing characteristics of the pulse sequence.

31. A method according to claim 30 wherein the timing characteristics include the mark and/or space durations of successive pulses.

32. A method according to claim 28 wherein the storing step comprises for storing respective time period values for successive pulses to be generated in a number of addressable storage locations, the time period values of defining the mark and/or space periods of successive pulses.

33. A method of generating a sequence of muscle stimulating pulses in accordance with pulse interval data held a memory comprising the steps of
   (A) reading out an item of pulse interval data from said memory;
   (B) initializing the contents of a memory location with data representing a count;
   (C) periodically incrementing or decrementing said contents;
   (D) periodically testing said contents and repeating (C) until said contents have a value determined in relation to the pulse interval data such that the number of repeats of (C) is determined by the pulse interval data; and
   (E) generating a stimulating pulse when said value occurs;
steps (A) to (E) inclusive being executed for each of a series of items of pulse interval data.

34. A method according to claim 33 wherein in step (B) the contents of the memory location are initialized with the value of the item of pulse interval data and wherein the loop from step (D) to step (E) is excited when said contents have a predetermined value.

35. A method according to claim 33 wherein a plurality of channels of stimulating pulses are produced.

36. A method according to claim 35 wherein steps (A) to (E) inclusive are carried out for each of a plurality of channels, corresponding steps for each channel being carried out in succession.

37. A method according to claim 33 and including the step of checking whether a stimulating pulse should be produced and inhibiting the production of a stimulating pulse if it should not be.

* * * * *